US008445192B2

(12) United States Patent
Gandini et al.

(10) Patent No.: US 8,445,192 B2
(45) Date of Patent: May 21, 2013

(54) DEVICE AND METHOD FOR DETECTION AND IDENTIFICATION OF IMMUNOLOGICAL PROTEINS, PATHOGENIC AND MICROBIAL AGENTS AND CELLS

(71) Applicants: Alberto Gandini, Emeryville, CA (US); James F. Antaki, Allison Park, PA (US)

(72) Inventors: Alberto Gandini, Emeryville, CA (US); James F. Antaki, Allison Park, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 0 days.

(21) Appl. No.: 13/684,618

(22) Filed: Nov. 26, 2012

(65) Prior Publication Data
US 2013/0078620 A1 Mar. 28, 2013

Related U.S. Application Data

(63) Continuation-in-part of application No. 13/590,859, filed on Aug. 21, 2012.

(60) Provisional application No. 61/539,210, filed on Sep. 26, 2011.

(51) Int. Cl.
*C12Q 1/70* (2006.01)

(52) U.S. Cl.
USPC ............................................................ 435/5

(58) Field of Classification Search
None
See application file for complete search history.

(56) References Cited

U.S. PATENT DOCUMENTS 3,714,037 A * 1/1973 Almasi et al. ................ 210/695
2010/0273184 A1 * 10/2010 Bar et al. ...................... 435/7.2

* cited by examiner

*Primary Examiner* — NC Yang
*Assistant Examiner* — Richard Moerschell
(74) *Attorney, Agent, or Firm* — Acker Wood IP Law, LLC; Gwen R. Acker Wood

(57) ABSTRACT

The present invention provides a method and device for detecting and quantifying the concentration of magnetic-responsive micro-beads dispersed in a liquid sample. Also provided is a method and microfluidic immunoassay pScreen™ device for detecting and quantifying the concentration of an analyte in a sample medium by using antigen-specific antibody-coated magnetic-responsive micro-beads. The methods and devices of the present invention have broad applications for point-of-care diagnostics by allowing quantification of a large variety of analytes, such as proteins, protein fragments, antigens, antibodies, antibody fragments, peptides, RNA, RNA fragments, functionalized magnetic micro-beads specific to $CD^{4+}$, $CD^{8+}$ cells, malaria-infected red blood cells, cancer cells, cancer biomarkers such as prostate specific antigen and other cancer biomarkers, viruses, bacteria, and other pathogenic agents, with the sensitivity, specificity and accuracy of bench-top laboratory-based assays.

29 Claims, 15 Drawing Sheets

DEVICE AND METHOD FOR DETECTION AND IDENTIFICATION OF IMMUNOLOGICAL PROTEINS, PATHOGENIC AND MICROBIAL AGENTS AND CELLS

CROSS REFERENCE TO RELATED APPLICATIONS

The present application is a continuation-in-part application of U.S. patent application Ser. No. 13/590,859, filed Aug. 21, 2012, which claims priority to U.S. Provisional Patent Application No. 61/539,210, filed Sep. 26, 2011, both of which are incorporated by reference herein in their entirety.

FIELD OF THE INVENTION

The present invention relates to the field of immunoassay and microfluidic devices and, in particular, to a point-of-care diagnostic method and device for the detection and quantification of magnetic-responsive micro-beads conjugated with proteins, cells and microbial agents dispersed in a liquid sample.

BACKGROUND OF THE INVENTION

Current immunoassay technologies for the detection and quantification of proteins rely on the specificity of the chemical interaction between antigens and antigen-specific antibodies. These tests may be classified into two main groups: laboratory based-tests and point-of-care (POC) tests. Laboratory-based tests are sensitive and accurate, but require a laboratory setting and skilled technicians. POC tests are designed to be used in the field and require limited training, but they are far less sensitive and accurate with most POC tests providing only binary positive/negative or semi-quantitative results.

All current immunoassay technologies involve the formation of an antigen-antibody complex. The detection of the complex indicates the presence of a targeted analyte in a sample. The antigen-antibody complex is detected by measuring the emission and/or reflection of light by the complex, when fluorescent-tagged antigen-specific antibodies are employed, or in the case in which antibody-coated micro-beads are used, by measuring the emission and/or reflection of light, or the magnetic moment of the micro-beads forming the antigen-bead complex. In all cases, optical or magnetic detectors and electronic readers are required.

For example, the simplest, best known and widely used POC diagnostic assay is the lateral flow assay, also known as the immunochromatic test. In this test, the targeted analyte is bound to an analyte-specific antibody linked to latex or gold nanoparticles. The presence of the analyte in the sample then is revealed by the formation of a visible band, or line, which results from the agglutination or accumulation of the analyte-antibody-linked complex. The band typically is visible macroscopically to the naked eye. Devices to increase the assay's sensitivity have been developed which can read color changes with microscopic sensitivity. Fluorescent or magnetic-labeled particles also have been used. In these cases, however, electronic readers to assess test results are needed. Thus, although sensitivity of the assay may increase, the cost and complexity of the assay also increases.

In recent years, antibody-coated micro-beads have been increasingly used for the separation and detection of proteins. In the field of immunoassay diagnostics, the concentration of micro-beads is a proxy for the concentration of targeted proteins in a sample. In these applications, it is necessary to identify the concentration of micro-beads in the sample solution. The micro-beads may be made magnetically responsive by adding a magnetic core or layer to a polymer bead. The micro-beads then may be coated with a variety of molecules and proteins, referred to as ligands, which serve the purpose of binding the targeted antigen via an antibody-antigen interaction. In addition, fluorescent dyes can be incorporated into the micro-beads making them optically detectable. Recently, a diagnostic test for the protein troponin using magnetic micro-beads has been proposed by Dittmer et al. (Philips Research Europe). In this assay, micro-beads coated with anti-troponin antibody are immobilized via antibody-troponin-antibodies on the surface of a micro-well with the aid of an applied magnetic field. The number of antibody-troponin-antibodies is measured by illuminating the bottom of the well and measuring the light reflected by the immobilized micro-beads with an optical receiver. Methods for the detection of *E. coli* also have been developed using immuno-magnetic micro-beads. In this case, the bacteria in the sample are measured by detecting time-resolve fluorescence.

While micro-bead technology has matured in the last decade, the technology to quantify micro-bead concentration has lagged behind. Current methods include manual microscopes and automatic or semi-automatic cell counters. Typically, micro-bead counting using a microscope involves the manual, and often tedious, counting of beads through a microscope objective. This method requires skilled technicians in a laboratory setting, is time consuming and is subject to a technician's interpretation. Cell counters require photo sensors to detect micro-beads automatically by measuring the light reflection of a laser beam hitting the micro-bead's surface. Cell counters, while accurate, are expensive and also require skilled technicians in sophisticated laboratory settings. Lab-on-a-chip devices to detect and measure the concentration of protein-coated micro-bead concentration also have been developed. These devices, however, rely on traditional approaches, i.e., light reflection and detection using micro-scale light and photo sensors and micro-scale magneto-resistance magnetometers. Thus, while greatly reducing the need for a laboratory setting and equipment, lab-on-a-chip devices still require electrical readers and transducers. In addition, these devices typically include handset and consumable components, resulting in increased manufacturing, calibration and maintenance costs. Thus, these devices have limited applications in the field of POC immunoassay diagnostics.

There exists a need, therefore, for a POC immunoassay device which has the sensitivity and specificity of laboratory-based immunoassay tests while being simple to use and low cost, as well as for methods to detect and quantify magnetic-responsive micro-bead concentration in a sample specimen.

SUMMARY OF THE INVENTION

The pScreen™ microfluidic immunoassay device, based on the inventions disclosed herein, fulfills all of the above-described needs in a single device. The detection and quantification of an unknown concentration of analyte in a liquid sample is obtained by exploiting the fluid-dynamic properties of magnetic-responsive micro-beads in liquid solution rather than using optical effects or magnetic field sensing as in current technologies. The unknown concentration of the target analyte is derived by measuring the differential flow rate between the sample flow in two micro-channels, one of which is under the influence of an applied magnetic field gradient. The present invention significantly reduces the cost and complexity of current laboratory-based immunoassay diagnostic tests, and greatly increases one-thousand fold the sensitivity of lateral flow tests, while maintaining the specificity and accuracy of laboratory-based tests, and the ability to detect targeted antigen concentration over a predefined range.

In an embodiment of the present invention, there is provided a method of detecting and quantifying the concentration of magnetic-responsive micro-beads in a fluid. The method comprises measuring flow rate ($Qm$) of a fluid in at least one test micro-channel ($Cm$) exposed to a magnetic field gradient with flow rate ($Qo$) of the fluid in a calibration micro-channel ($Co$) not exposed to a magnetic field gradient, in which the micro-channels are kept at an equal and constant pressure, calculating the ratio $Qm/Qo$, the difference $Qo-Qm$, and the ratio $(Qo-Qm)^p/(Qm)^q$, wherein p and q are derived through a calibration process, wherein the ratios $Qm/Qo$ and $(Qo-Qm)^p/(Qm)^q$ are a proxy for the number of magnetic-responsive micro-beads in the fluid, and then quantifying the concentration of magnetic-responsive micro-beads in the fluid. The presence of magnetic-responsive micro-beads in the at least one test micro-channel which is exposed to the magnetic field gradient causes flocculation of the magnetic-responsive micro-beads in the fluid which reduces the flow rate of the fluid through the at least one test micro-channel.

In another embodiment, there is provided a method for detecting and quantifying concentration of an analyte in a liquid sample. The method comprises adding a liquid sample to a liquid sample inlet of a reaction chamber. The reaction chamber has adsorbed on its surface a plurality of immobilized antigen-specific antibodies (Ab1) specific to an analyte. The surface of the reaction chamber also has a plurality of magnetic-responsive micro-beads desiccated thereon, in which each of the plurality of magnetic-responsive micro-beads is coated with an antigen-specific antibody (Ab2) specific to the analyte. The method comprises having the liquid sample incubate within the reaction chamber, which causes rehydration of the plurality of antibody-coated magnetic-responsive micro-beads as the liquid sample is added and agitated in the reaction chamber, which rehydration disperses the antibody-coated magnetic-responsive micro-beads in the liquid sample, binding the rehydrated antibody-coated magnetic-responsive micro-beads as well as the antigen-specific antibodies immobilized on the surface of the reaction chamber to any analyte present in the liquid sample to form Ab1-analyte-Ab2-coated magnetic-responsive micro-bead complexes on the surface of the reaction chamber, having the liquid sample containing any unbound antibody-coated magnetic-responsive micro-beads exit the reaction chamber through a chamber outlet and transfer through a continuous fluid connection to a micro-channel splitter which bifurcates to form a calibration micro-channel ($Co$) and at least one test micro-channel ($Cm$). The at least one test micro-channel and the calibration micro-channel are kept at an equal and constant pressure. The calibration micro-channel is in continuous fluid connection with a graduated column, and the at least one test micro-channel is in continuous fluid connection with at least one graduated column. Each of the graduated columns has a graduated scale thereon. The method comprises measuring flow rate ($Qm$) of the liquid sample in the at least one test micro-channel exposed to a magnetic field gradient with flow rate ($Qo$) of the fluid in the calibration micro-channel not exposed to a magnetic field gradient, in which the presence of any unbound antibody-coated magnetic-responsive micro-beads in the at least one test micro-channel which is exposed to the magnetic field gradient causes flocculation of the antibody-coated magnetic-responsive micro-beads in the liquid sample which reduces the flow rate of the liquid sample through the at least one test micro-channel, calculating the ratio $Qm/Qo$, the difference $Qo-Qm$, and the ratio $(Qo-Qm)^p/(Qm)^q$, wherein p and q are derived through a calibration process, wherein the ratios $Qm/Qo$ and $(Qo-Qm)^p/(Qm)^q$ are a proxy for the number of magnetic-responsive micro-beads in the liquid sample, which is a proxy for the concentration of analyte in the liquid sample, and then quantifying the concentration of analyte in the liquid sample.

In a further embodiment of the present invention, there is provided a single use, portable, lab-on-card microfluidic pScreen™ magnetic-responsive micro-bead concentration counter device for detecting and quantifying the concentration of magnetic-responsive micro-beads in a liquid sample. The microfluidic device is comprised of a liquid sample inlet defined by an opening for accepting a liquid sample that contains a quantity of magnetic-responsive micro-beads. The liquid sample inlet is in continuous fluid connection with a flow resistor, which is in continuous fluid connection with a micro-channel splitter which bifurcates to form a calibration micro-channel ($Co$) and at least one test micro-channel ($Cm$). The calibration micro-channel and the at least one test micro-channel are kept at an equal and constant pressure. The calibration micro-channel is in continuous fluid connection with a graduated column, and the at least one test micro-channel is in continuous fluid connection with at least one graduated column. The at least one test micro-channel is exposed to a magnetic field gradient, which causes flocculation of the magnetic-responsive micro-beads in the at least one test micro-channel. The flocculation reduces the flow rate ($Qm$) of the liquid sample in the at least one test micro-channel compared to the flow rate ($Qo$) of the liquid sample in the calibration micro-channel. Each of the graduated columns has a graduated scale thereon which provides a read-out of the total volume of the liquid sample collected in each of the graduated columns, in which the total volume of the liquid sample collected in the at least one test micro-channel graduated column indicates the concentration of magnetic-responsive micro-beads in the liquid sample.

In yet another embodiment of the invention, there is provided a single use, portable, lab-on-card microfluidic pScreen™ immunoassay device for detecting and measuring an analyte in a liquid sample. The microfluidic immunoassay device is an assembly of the microfluidic pScreen™ device described above and an immunoassay reaction chamber.

In particular, the microfluidic pScreen™ immunoassay device comprises a liquid sample inlet defined by an opening for accepting the liquid sample. The liquid sample inlet is in continuous fluid connection with a flow resistor channel, which is in continuous fluid connection with an assay inlet of a reaction chamber. The reaction chamber has adsorbed on its surface a plurality of immobilized antigen-specific antibodies (Ab1) specific to an analyte, as well as having a plurality of magnetic-responsive micro-beads desiccated thereon. Each of the plurality of magnetic-responsive micro-beads is coated with an antigen-specific antibody (Ab2) specific to the analyte. Flow of the liquid sample through the reaction chamber rehydrates the plurality of antibody-coated magnetic-responsive micro-beads which disperses into the liquid sample. Any analyte present in the liquid sample binds to the dispersed antibody-coated magnetic-responsive micro-beads as well as to the antigen-specific antibodies immobilized on the surface of the reaction chamber to form Ab1-analyte-Ab2-coated magnetic-responsive micro-bead complexes. Any unbound antibody-coated magnetic-responsive micro-beads exit the reaction chamber through an assay outlet, which is in continuous fluid connection with a micro-channel splitter that bifurcates to form a calibration micro-channel (Co) and at least one test micro-channel (Cm), which are kept at an equal and constant pressure. The calibration micro-channel is in continuous fluid connection with a graduated column, and the at least one test micro-channel in continuous fluid connection with at least one graduated column. The at least one test micro-channel is exposed to a magnetic field gradient, which causes flocculation of the magnetic-responsive micro-beads in the at least one test micro-channel. The flocculation reduces the flow rate (Qm) of the liquid sample in the at least one test micro-channel compared to the flow rate (Qo) of the liquid sample in the calibration micro-channel. Each of the graduated columns has a graduated scale thereon which provides a read-out of the total sample volume collected in each of the graduated columns, in which the total sample volume collected in the at least one test micro-channel graduated column indicates the concentration of analyte in the liquid sample.

As described above, the ratios Qm/Qo and $(Qo-Qm)^p/(Qm)^q$ are a proxy for the number of magnetic-responsive micro-beads in a liquid sample, which is a proxy for the concentration of analyte in the liquid sample.

The devices may be fabricated by methods which include, without limitation, etching each of the micro-channels on a plastic substrate using a laser etcher system and then sealing the top of each of the micro-channels in plastic by thermal bonding, and by injection mold casting in plastic. Suitable plastic substrates, plastic sealing and injection mold casting plastics include, without limitation, poly(ethylene terephthalate) glycol, poly(lactic-co-glycolic acid) and poly(methyl methacrylate), respectively.

Liquid samples that can be assayed in accordance with the embodiments of the invention include, without limitation, water, plasma, serum, buffer solution, urine, whole blood, blood analogs, and liquid solutions from dilution of solid biological matter or other biological fluids.

Analytes that can be detected and quantified in accordance with the embodiments of the invention include, without limitation, proteins, protein fragments, antigens, antibodies, antibody fragments, peptides, RNA, RNA fragments, functionalized magnetic micro-beads specific to $CD^{4+}$, $CD^{8+}$ cells, malaria-infected red blood cells, cancer cells, cancer biomarkers such as prostate specific antigen and other cancer biomarkers, viruses, bacteria such as E. coli or other pathogenic agents.

The magnetic field gradient in accordance with the invention is generated from two magnets aligned lengthwise with the at least one test micro-channel and along opposite poles to expose the at least one test micro-channel to the magnetic field gradient. The at least one test micro-channel is located between a gap formed between the opposite poles of the magnets. In another embodiment, the magnetic field gradient is generated by one magnet and a magnetic-responsive structure positioned near the at least one test micro-channel.

In accordance with the invention, the magnetic field generated can range between about 0.05 Tesla (T) to about 0.5 T, and the magnetic field gradient that is generated can be about 10 T/m or greater.

The total sample volume collected in the calibration micro-channel graduated column serves as a control for parameters such as variation in viscosity between samples, level of hematocrit in blood samples, temperature and humidity fluctuations and sample volumes.

In one embodiment of the invention, the micro-channel splitter of the microfluidic devices bifurcates to form one test micro-channel and one calibration micro-channel.

In another embodiment of the invention, the micro-channel splitter of the microfluidic device bifurcates to form three test micro-channels and one calibration micro-channel, in which each of the three test micro-channels is in continuous fluid connection with one graduated column.

In another embodiment of the invention, the micro-channel splitter of the microfluidic device bifurcates to form four test micro-channels and one calibration micro-channel, in which the four test micro-channels merge to be in continuous fluid connection with one graduated column.

The present invention will be more fully understood from the following description of the invention and by reference to the figures and claims appended hereto.

BRIEF DESCRIPTION OF THE DRAWINGS

A fuller understanding of the invention can be gained from the following description when read in conjunction with the accompanying drawings in which.

DETAILED DESCRIPTION OF THE INVENTION

As used herein, the terms "magnetic-responsive micro-beads," "magnetic micro-beads" and "micro-beads" are meant to be interchangeable.

As used herein, the terms "analyte" and "antigen" are meant to be interchangeable.

As used herein, the terms "calibration micro-channel(s)" and "control micro-channel(s)" are meant to be interchangeable.

Figure 1:
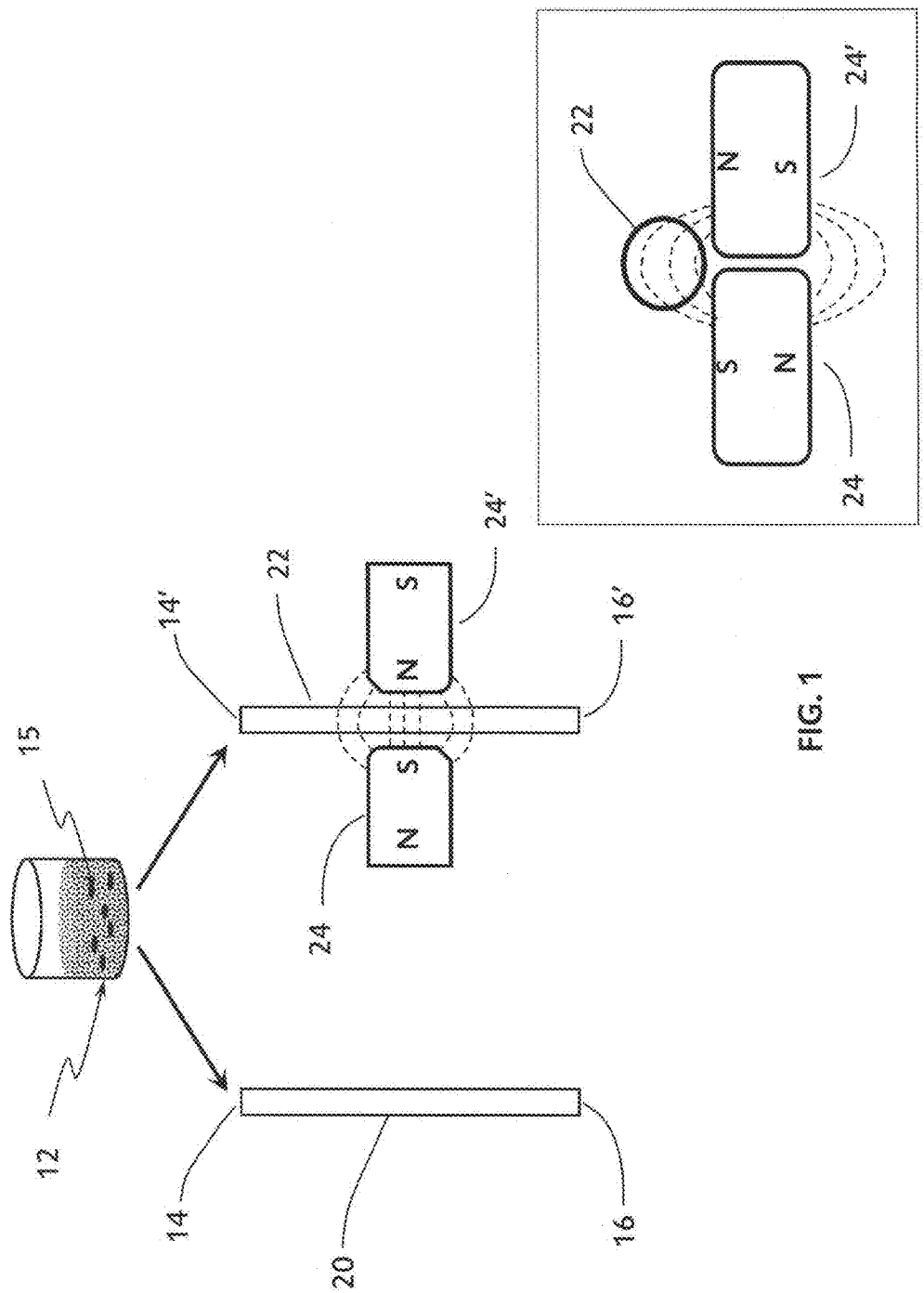
FIG. 1 is a schematic illustration of the method for determining the number of magnetic-responsive micro-beads in a fluid, in which the ratio between the flow rate in the calibration micro-channel (Co) and the test micro-channel (Cm) is measured, according to the embodiments of the invention.

The present invention provides a flow rate-based method for detecting and quantifying the concentration, i.e., number, of magnetic-responsive micro-beads in a fluid. The ratio, Qm/Qo, between the flow rate (Qm) in a test micro-channel (Cm) exposed to a localized high-gradient magnetic field, and the unperturbed flow rate (Qo) in a calibration, or control, micro-channel (Co) not exposed to the localized high-gradient magnetic field, is a monotonic function of the number of magnetic-responsive micro-beads flowing through the test micro-channel. That is:

$$Qm(N_m)/Qo = f(N_m) \qquad \text{Equation (1)}$$

where Nm is the total number of magnetic-responsive micro-beads transported by the fluid into the localized high-magnetic field region. Both micro-channels are held at an equal and constant pressure. As shown in FIG. 1, a fluid 12 seeded with magnetic-responsive micro-beads 15 flows into two micro-channel inlets 14, 14' and out of two micro-channel outlets 16, 16'. The test micro-channel 22 on the right is exposed to a high-gradient magnetic field generated by two magnets 24, 24'. The magnets are positioned as shown in FIG. 1 and in the inset. In an embodiment, the magnetic field gradient is generated by one magnet and a magnetic-responsive structure (not shown) positioned near the test micro-channel 22. A magnetic-responsive structure may be made of a metallic material with ferromagnetic, super-paramagnetic or paramagnetic properties, such that upon application of an external magnetic field the magnetic-responsive structure generates an induced magnetic field. The structure is geometrically shaped, e.g., cylindrically-shaped, in order to generate a magnetic field gradient in the region occupied by the test micro-channel. Equation 1 applies to a wide range of magnetic-responsive micro-bead concentrations, ranging from about 50 micro-beads/µl to about $2 \times 10^6$ micro-beads/µl. The upper and lower limits, however, are a function of the micro-channels' size and magnetic field topology. Hence, both upper and lower limits may vary based on these parameters.

Because f(Nm) is a monotonic function of Nm, it also holds that:

$$N_m = f^{-1}(Qm(N_m)/Qo). \qquad \text{Equation (2)}$$

Thus, according to Equation 2, the number of magnetic-responsive micro-beads in a given fluid is a monotonic function of the ratio Qm/Qo. Thus, the number of magnetic-responsive micro-beads can be determined by measuring the ratio Qm/Qo in the two micro-channels, configured as shown in FIG. 1. In other words, the ratio Qm/Qo is a specific proxy for the number of magnetic-responsive micro-beads in a given fluid.

The analytical form of the function depends on the geometry, i.e., length and inner diameter of the two micro-channels, magnetic field topology, and the size of the magnetic-responsive micro-beads. In addition, the difference $Q_o - Q_m$, and the ratio $(Q_o - Q_m)^p/(Q_m)^q$, where p and q are derived through a calibration process, are a proxy for the number of magnetic-responsive micro-beads in the fluid. The parameters p and q are obtained as followed. A solution containing a known concentration of micro-beads and of known volume is passed through the micro-channels and the flow rate Qm and Qo are measured. Then, a solution containing the same concentration of magnetic-responsive micro-beads but of larger volume similarly is passed through the micro-channels. This process is repeated several times. Then, the ratio $(Qo-Qm)^p/(Qm)^q$, with p and q set equal to 1, are plotted versus the volume of each sample. Using the well-known least square regression method, p and q are determined by enforcing the condition that the ratios $(Qo-Qm)^p/(Qm)^q$ versus sample volume form a horizontal straight line with slope equal to zero.

The present invention further provides a microfluidic pScreen™ magnetic-responsive micro-bead concentration counter device for detecting and quantifying magnetic-responsive micro-bead concentration in a liquid sample. This device leverages the previously described flow rate-based detection and quantification method.

Figure 2:
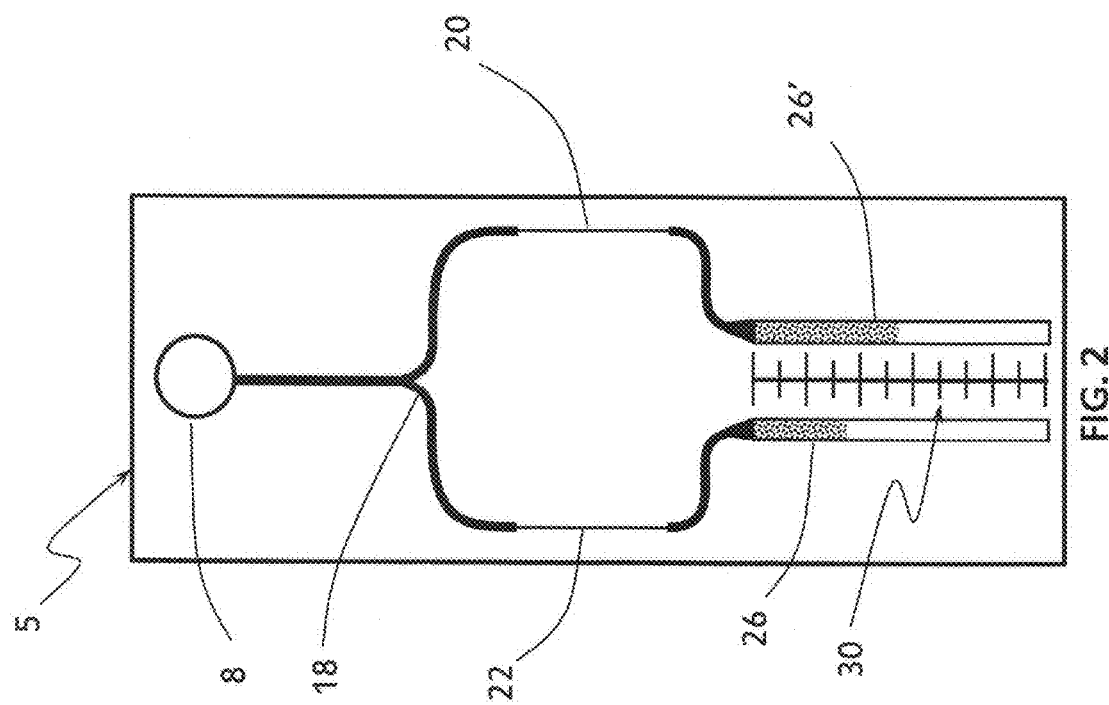
FIG. 2 is a schematic illustration of the microfluidic pScreen™ magnetic-responsive micro-bead concentration counter device, having one test micro-channel and one calibration micro-channel, according to the embodiments of the invention.
Figure 3:
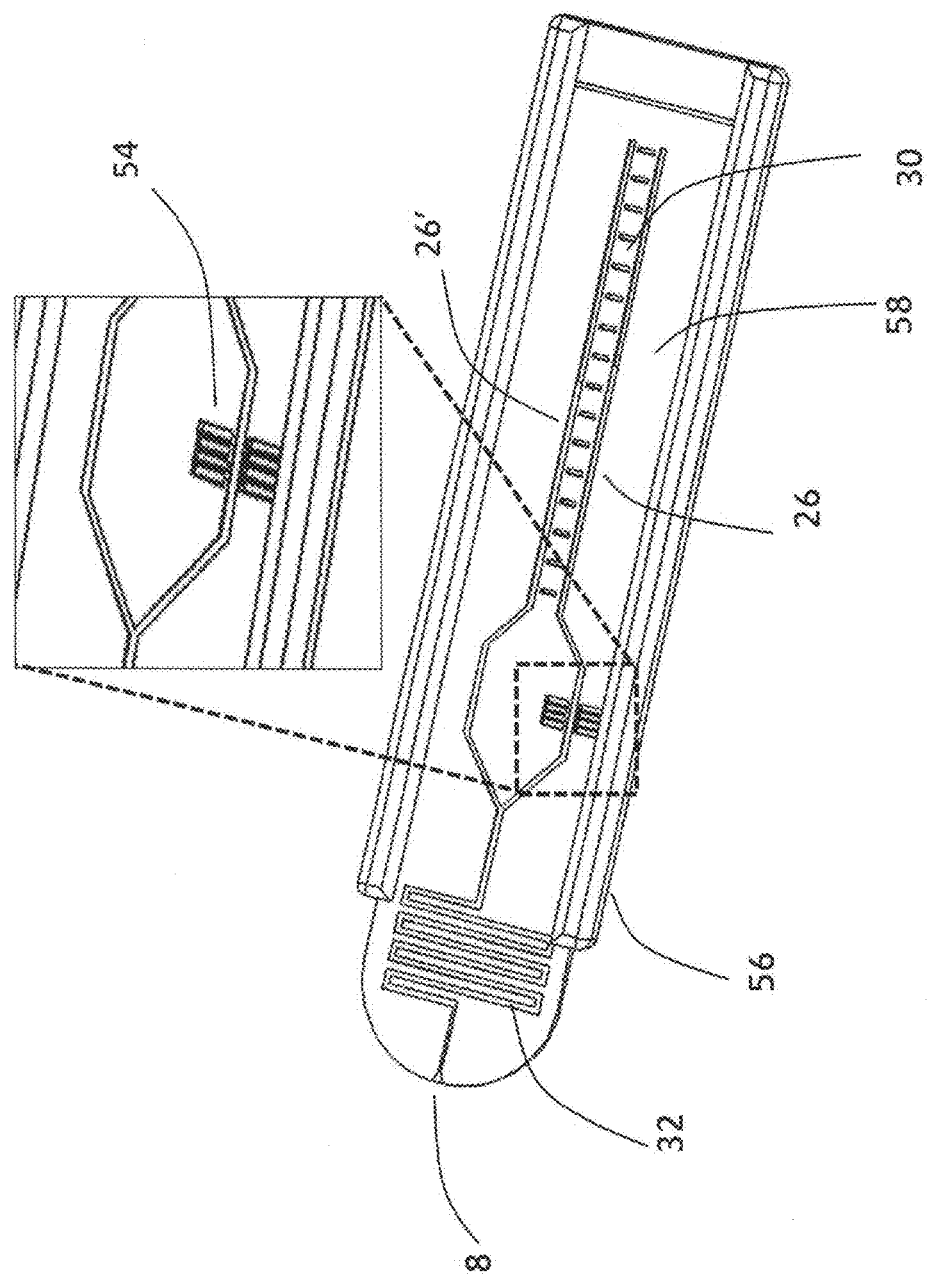
FIG. 3 is an artistic rendering of the microfluidic pScreen™ immunoassay device, according to the embodiments of the invention.

FIGS. 2 and 3 show the pScreen™ microfluidic device 5 for the detection and quantification of magnetic-responsive magnetic beads in a liquid sample of the present invention. The microfluidic device 5 comprises a liquid sample inlet 8 in which a liquid sample, or specimen, which contains an unknown amount of magnetic-responsive micro-beads, is applied. From the liquid sample inlet 8, the liquid sample, self-propelled by capillary action, flows through a flow resistor 32 (shown in FIG. 3) and enters a micro-channel splitter 18. The micro-channel splitter 18 bifurcates into two smaller micro-channels: a calibration micro-channel 20 and a test micro-channel 22. The two micro-channels 20, 22 are identical in length and inner diameter (best shown in FIG. 2).

The concentration of magnetic-responsive micro-beads that can be detected and quantified using the methods and devices of the invention is about 50 micro-beads/µl to about $2 \times 10^6$ micro-beads/0; and the diameter of the magnetic-responsive micro-beads is about 0.2 µm to about 20 µm. In an embodiment, the diameter of the magnetic micro-beads is about 4.0 µm.

In accordance with the invention, the test micro-channel and the calibration micro-channel are made of a capillary tube, in which the length of the capillary tube is about 0.2 cm to about 20 cm. In an embodiment, the length of the capillary tube is about 3.0 cm to about 7.5 cm. In another embodiment, the length of the capillary tube is about 1.5 cm.

In an embodiment, the length of the calibration micro-channel 20 and the test micro-channel 22 is about 0.2 cm to about 20 cm. In another embodiment, the length of the two micro-channels 20, 22 is about 3.0 cm to about 7.5 cm. In still another embodiment, the length of the two micro-channels 20, 22 is about 1.5 cm.

In an embodiment, the inner diameter of the calibration micro-channel 20 and the test micro-channel 22 is about 50 μm to about 500 μm. In another embodiment, the inner diameter of the two micro-channels 20, 22 is about 50 μm.

A magnetic field gradient is applied only to the test micro-channel 22. The magnetic field gradient is generated by small rare-earth (e.g., neodymium) permanent magnet and ferromagnetic (e.g., nickel, iron) pole structures (not shown) which serve as a magnetic concentrator 54 (shown in FIG. 3) specifically designed to concentrate the magnetic field, hence creating a high magnetic field gradient (of about 100 T/m). In the calibration channel 20, the liquid sample flows freely at a very low velocity (Reynolds number around 1) and shear rate range (1 to 400 s$^{-1}$). In the test micro-channel 22, the magnetic field gradient induces micro-bead flocculation if magnetic-responsive micro-beads are present in the sample. Even in very small concentrations, as low as <50 micro-beads/μl, the flow rate through the test micro-channel 22 will be reduced due to the formation of the magnetically-induced micro-bead flocculation. After flowing through the calibration and test micro-channels 20, 22, a volume of liquid sample is collected in two graduated columns 26, 26', both of equal size and volume.

Each graduated column 26, 26' has a graduated scale thereon 30 which provides an easy to interpret read-out system of the total sample volume collected in each graduated column 26, 26'. The graduated columns' 26, 26' length and cross section, as well as the respective scales 30 thereon, are designed to be visible to the naked eye. Unlike current POC read-out devices, the read-out system of the microfluidic device of the present invention does not require electrical transducers and/or sensors. As shown in FIGS. 2 and 3, both graduated columns 26, 26' are clearly visible. As shown in FIG. 3, the microfluidic device 5 may be configured in a cartridge 58 which fits into a holder 56. The read-out obtained by the microfluidic device 5 can be determined at any time by direct comparison of the fluid in the two graduated columns 26, 26'.

Referring now to FIG. 2, the micro-channel configuration provides for the concentration of micro-beads to be a monotonic function only of the volumes Vo and Vm (Vo and Vm are the volumes collected at the micro-channel outlets 16, 16' of the calibration micro-channel 20 (Co) and test micro-channel 22 (Cm), respectively; shown in FIG. 1). This approach allows the user to read out the result provided by the pScreen™ microfluidic device of the present invention at any time while the assay is running or at any time after the assay has been completed.

Given the relationship in Equation (1), and because the flow rate in the calibration micro-channel 20 is constant and the magnetic-responsive micro-beads are uniformly distributed in the sample fluid, and by definition ρ=dN/dV and dV=Qdt, where N is the number of micro-beads, Q the flow rate, and V the fluid volume, the below equations are satisfied at any time instances:

$$t = \int_0^{N_o} \frac{dN'}{\rho Q_0} = \frac{N_0}{\rho Q_0},$$ Equation (3)

$$t = \int_0^{N_m} \frac{dN'}{\rho Q_m}.$$ Equation (4)

where, t is the time, ρ is the magnetic-responsive micro-bead concentration in the sample specimen 12, Qo and Qm are the flow rates in the calibration and test micro-channels 20, 22, respectively, No and Nm is the number of magnetic-responsive micro-beads passing through the calibration and test micro-channels 20, 22, respectively, and the prime symbol inside the integral, dN', indicates, according to standard convention, that the integral operation is computed on N variable It thus follows that:

$$N_0 = g(N_m),$$ Equation (5)

$$\text{with}: g(N) \equiv \int_0^{N_m} \frac{dN'}{Q(N)},$$

$$\text{and}: Q = \frac{Q_m}{Q_0}.$$

Thus:

$$N_m = g^{-1}(N_0).$$ Equation (6)

Since, $$N_0 = \rho V_0,$$ Equation (7)

and $N_m = \rho V_m$, we have that: $\rho V_m = g^{-1}(\rho V_0)$

Hence:

$$\rho = F(V_0, V_m).$$ Equation (8)

Thus, the pScreen™ microfluidic device of the present invention provides a comparative read-out system in which the magnetic-responsive micro-bead concentration, ρ, is a monotonic function of only Vm, the volume flowing through the test micro-channel 22 where the magnetic-induced flocculation forms and Vo, the volume flowing through the calibration micro-channel 20 without the magnetic-induced flocculation.

The comparative read-out system of the pScreen™ microfluidic device of the present invention greatly simplifies the detection and quantification of magnetic-responsive micro-bead concentration in a liquid sample. In addition, this comparative read-out system has the significant advantage of virtually eliminating common-mode error (with the calibration graduated column 26 acting as a control), such as variation in viscosity between samples, level of hematocrit in blood samples, temperature and humidity fluctuation of the test environment, and sample volume. The pScreen™ microfluidic device of the present invention thus provides a stand-alone device for the detection and quantification of magnetic-responsive micro-bead concentration in liquid samples over a wide range of concentrations and micro-bead sizes.

Figure 4:
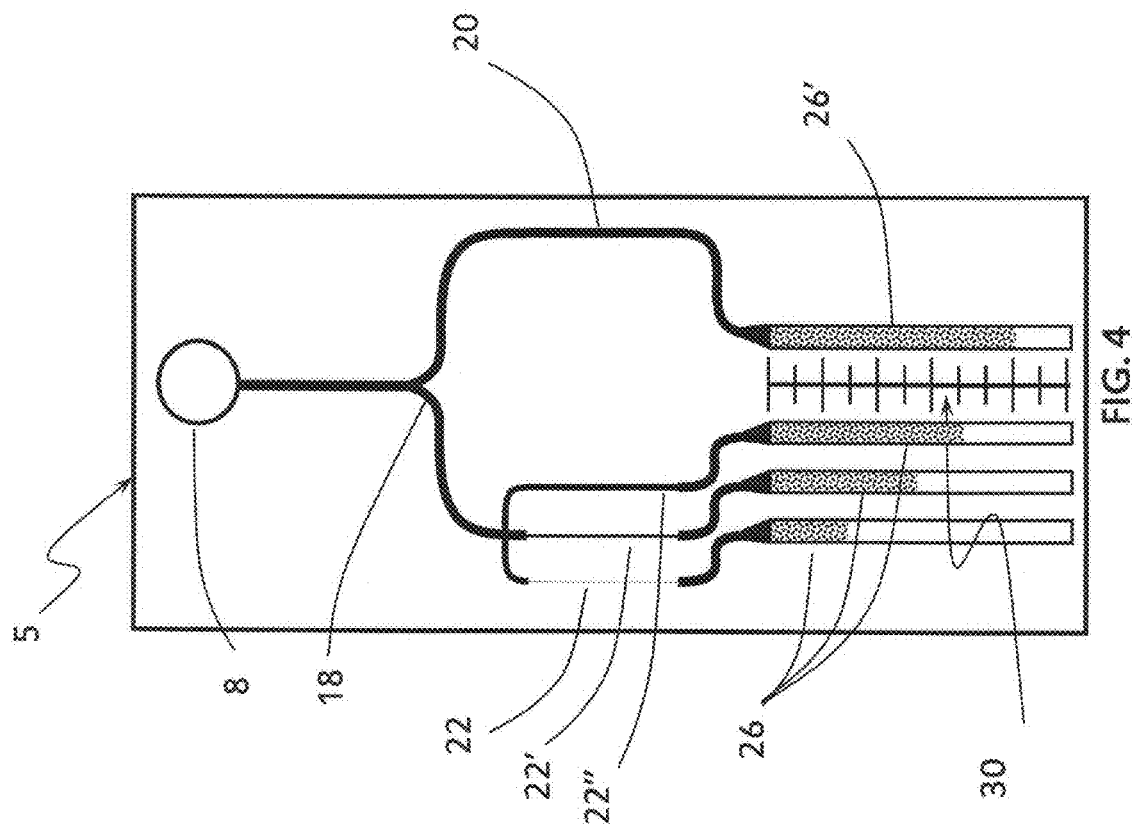
FIG. 4 is a schematic illustration of the microfluidic pScreen™ magnetic-responsive micro-bead concentration counter device, having three test micro-channels and one calibration micro-channel, according to the embodiments of the invention.

FIG. 4 shows an alternate embodiment of the microfluidic device 5 of the invention. In this embodiment, the test micro-channel (Cm) is split into three test micro-channels 22, 22' which 22" run parallel to one other. The three test micro-channels 22, 22' and 22" are of the same length but have a different inner diameter from one another. Each test micro-channel 22, 22', 22" is connected to a separate graduated column 26. In an embodiment, the first test micro-channel 22 has an inner diameter of about 50 μm to about 500 μm, the second test micro-channel 22' has an inner diameter of about 100 μm to about 250 μm, and the third test micro-channel 22" has an inner diameter of about 250 μm to about 5 mm. In another embodiment, the first test micro-channel 22 has an inner diameter of about 50 μm, the second test micro-channel 22' has an inner diameter of about 100 μm, and the third test micro-channel 22" has an inner diameter of about 250 μm. The inner diameter of the calibration micro-channel 20 is such that the area of the cross-section of the calibration micro-channel 20 is identical to the sum of the areas of the cross-sections of the three test micro-channels 22, 22', 22".

For a given amount of magnetic-responsive micro-beads entering each of the three test micro-channels 22, 22' 22", the third, largest test micro-channel 22" experiences the lowest reduction in flow rate, the second, middle-sized test micro-channel 22' experiences a reduction in flow rate greater than in the third, largest test micro-channel 22", and the first, smallest test micro-channel 22 experiences the greatest reduction in flow rate. In addition, the first, smallest test micro-channel 22 will tend to clog before the second, middle-sized test micro-channel 22' and the third, largest test micro-channel 22", and the middle-sized test micro-channel 22' will tend to clog before the largest test micro-channel 22". Hence, the device in accordance with this embodiment allows measurement of a wide range of concentrations of magnetic-responsive micro-beads, in which the first, smallest test micro-channel 22 allows for finely-tuned measurements of magnetic-responsive micro-beads at low concentrations and the third, largest test micro-channel 22" allows for gross measurements of magnetic-responsive micro-beads at high concentrations.

Figure 5:
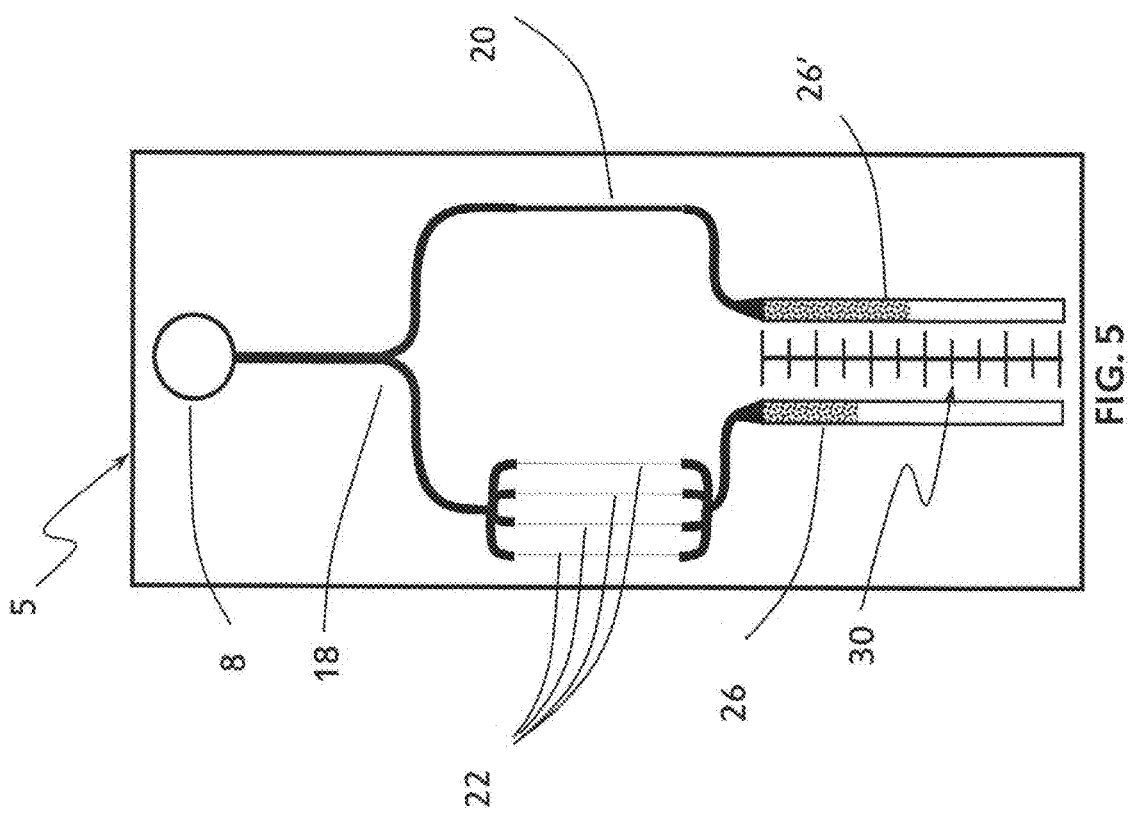
FIG. 5 is a schematic illustration of the microfluidic pScreen™ magnetic-responsive micro-bead concentration counter device, having four test micro-channels and one calibration micro-channel, according to the embodiments of the invention.

FIG. 5 shows an additional alternate embodiment of the invention. In this embodiment, the test micro-channel 22 (Cm) is split into four micro-channels which run parallel to each other. The four test micro-channels 22 have the same length and inner diameter. In an embodiment, each of the four test micro-channels has an inner diameter of about 12.5 μm to about 125 μm. In another embodiment, each of the four test micro-channels has an inner diameter of about 12.5 μm. The inner diameter of the calibration micro-channel 20 is such that the area of the cross-section of the calibration micro-channel 20 is identical to the sum of the areas of the cross-sections of the four test micro-channels 22, 22', 22".

The four test micro-channels 22 rejoin to connect to one graduated column 26. If no magnetic-responsive micro-beads flow into the four test-micro-channels 22 and the one calibration micro-channel 20, then the flow rate of the fluid through the calibration micro-channel 20 is the sum of the flow rates in each of the test micro-channels. Equations (1) through (8) also apply in this embodiment, however, because there are four parallel test micro-channels compared to one test micro-channel, a greater volume of fluid can flow through the device in a shorter amount of time, thus allowing a user to obtain a read out of results of the pScreen™ microfluidic device in a shorter period of time.

The present invention also provides a flow rate-based method for detecting and quantifying concentration of an analyte in a liquid sample. The analyte can include, without limitation, proteins, protein fragments, antigens, antibodies, antibody fragments, peptides, RNA, RNA fragments, cells, cancer cells, viruses, and other pathogenic agents.

The method according to this embodiment comprises adding a liquid sample to a liquid sample inlet of a reaction chamber. The reaction chamber has adsorbed on its surface a plurality of immobilized antigen-specific antibodies (Ab1) specific to an analyte. The surface of the reaction chamber also has a plurality of magnetic-responsive micro-beads desiccated thereon, in which each of the plurality of magnetic-responsive micro-beads is coated with an antigen-specific antibody (Ab2) specific to the analyte. The method comprises having the liquid sample incubate inside the reaction chamber, which causes rehydration of the plurality of antibody-coated magnetic-responsive micro-beads as the liquid sample is added and agitated in the reaction chamber, which rehydration disperses the antibody-coated magnetic-responsive micro-beads in the liquid sample, binding the rehydrated antibody-coated magnetic-responsive micro-beads as well as the antigen-specific antibodies immobilized on the surface of the reaction chamber to any analyte present in the liquid sample to form Ab1-analyte-Ab2-coated magnetic micro-bead complexes on the surface of the reaction chamber, having the liquid sample containing any unbound antibody-coated magnetic-responsive micro-beads exit the reaction chamber through a chamber outlet and transfer through a continuous fluid connection to a micro-channel splitter which bifurcates to form a calibration micro-channel (Co) and at least one test micro-channel (Cm). The at least one test micro-channel and the calibration micro-channel are kept at an equal and constant pressure. The calibration micro-channel is in continuous fluid connection with a graduated column, and the at least one test micro-channel is in continuous fluid connection with at least one graduated column. Each of the graduated columns has a graduated scale thereon. The method comprises measuring flow rate (Qm) of the liquid sample in the at least one test micro-channel exposed to a magnetic field gradient with flow rate (Qo) of the fluid in the calibration micro-channel not exposed to a magnetic field gradient, in which the presence of any unbound antibody-coated magnetic-responsive micro-beads in the at least one test micro-channel which is exposed to the magnetic field gradient causes flocculation of the antibody-coated magnetic-responsive micro-beads in the liquid sample which reduces the flow rate of the liquid sample through the at least one test micro-channel, and calculating the ratio Qm/Qo, the difference Qo−Qm, and the ratio $(Qo-Qm)^p/(Qm)^q$, wherein p and q are derived through a calibration process, and wherein the ratios Qm/Qo and $(Qo-Qm)^p/(Qm)^q$ are a proxy for the number of magnetic-responsive micro-beads in the liquid sample, which is a proxy for the concentration of analyte in the liquid sample.

Figure 6:
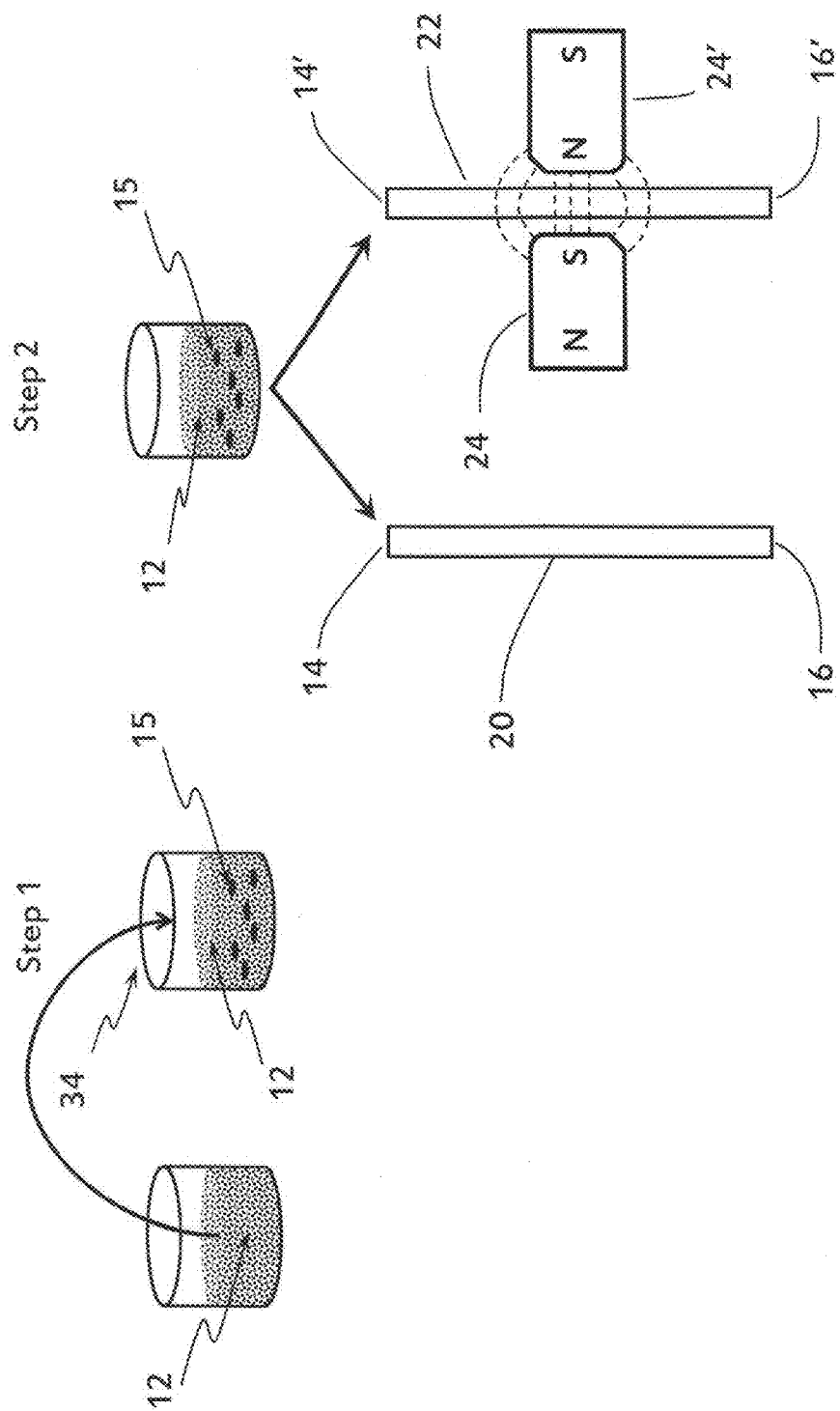
FIG. 6 is the schematic illustration of the method for determining the concentration of analyte in a fluid, in which the sample analyte is bound to immobilized analyte-specific immobilized antibodies and to analyte-specific coated magnetic-responsive micro-beads, the ratio $Q_m/Q_o$, of the flow rate $Q_o$ in the calibration micro-channel, Co, and the flow rate, $Q_m$, in the test micro-channel, Cm, is measured, according to the embodiments of the invention.

As shown in FIG. 6, a liquid sample 12 is added, Step 1, to a reaction chamber 34, which has adsorbed on its surface a plurality of immobilized antigen-specific antibodies (Ab1) (not shown) and contains a plurality of magnetic-responsive micro-beads coated with antigen-specific antibodies (Ab2) 15 desiccated on the surface of the reaction chamber 34. In Step 1, by adding the liquid sample to the reaction chamber 34, the antibody-coated magnetic-responsive micro-beads 15 are rehydrated and the magnetic-responsive micro-beads 15, as well as the antigen-specific antibodies immobilized on the surface of the reaction chamber 34, bind to any analyte present in the liquid sample 12 to form Ab1-analyte-Ab2-coated magnetic-responsive micro-bead complexes on the surface of the reaction chamber 34, with any unbound magnetic-responsive micro-beads 15 free to flow (Step 2) into two micro-channel inlets 14, 14' and out of two micro-channel outlets 16, 16'. The test micro-channel 22 on the right is exposed to a high-gradient magnetic field generated by two magnets 24. As described in the previous paragraph, the number of magnetic-responsive micro-beads in a liquid sample passing through two micro-channels, a test micro-channel (Co) and a calibration, or control micro-channel (Cm), is proportional to the ratio, $Q_m/Q_o$, between the flow rate (Qm) in a micro-channel (Cm) exposed to a localized high-gradient magnetic field, and the unperturbed flow rate (Qo) in a micro-channel (Co) not exposed to the localized high-gradient magnetic field. Therefore, by measuring the flow rates Qm and Qo, the concentration of analyte in the liquid sample can be determined. The method applies to a wide range of antigen concentration, from about 0.01 ng/ml to about 1 µg/ml.

The present invention further provides a pScreen™ microfluidic immunoassay device for the detection and quantification of proteins, protein fragments, antigens, antibodies, antibody fragments, RNA, RNA fragments, cells, cancer cells, viruses, and other pathogenic agents. This device leverages the previously described method for detecting and quantifying concentration of an analyte in a liquid sample.

Principle of Operation

Figure 7:
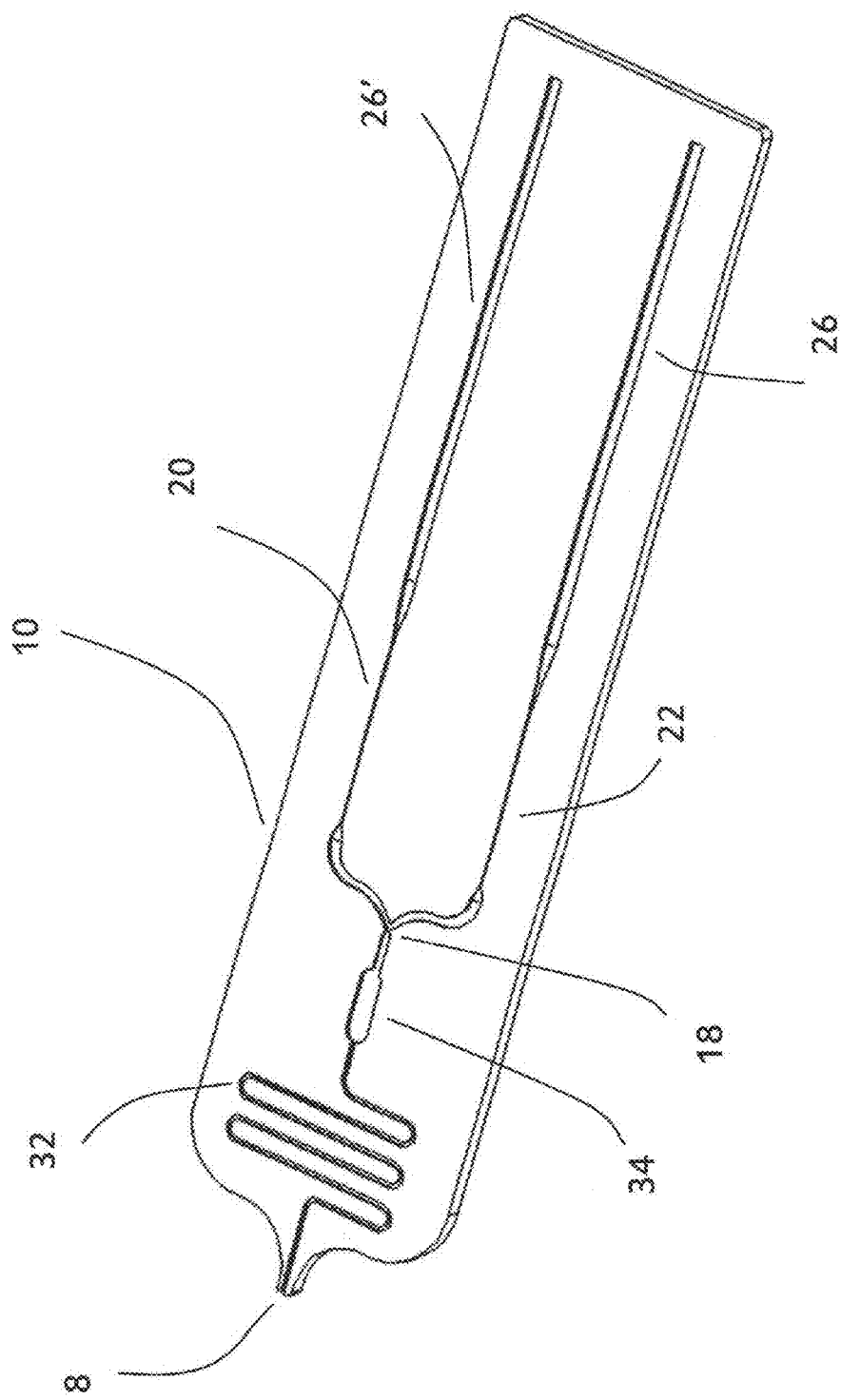
FIG. 7 is a schematic illustration of the pScreen™ immunoassay device, according to the embodiments of the invention.

In one embodiment of the invention, as shown in FIG. 7, the pScreen™ microfluidic immunoassay device 10 has a liquid sample inlet 8, a flow resistor channel 32, a reaction chamber 34, a micro-channel splitter 18, a test micro-channel 22, a calibration micro-channel 20 and graduated readout columns 26, 26'. In use, a liquid sample, or specimen, which may contain an unknown amount of a target analyte, is applied into the liquid sample inlet 8. By capillary action, the sample is self-propelled and transferred from the liquid sample inlet 8 into the reaction chamber 34 via the flow resistor channel 32. The flow rate of the liquid sample is determined by the cross-section and length of the flow resistor channel 32 and the surface tension of the device material and sample liquid, as well as by the binding kinetic reaction between the analyte, i.e., antigen, and antibody in the reaction chamber 34.

As shown in FIG. 8A, the reaction chamber 34 is coated with antigen-specific antibodies (Ab1) 46 immobilized onto the surface of the reaction chamber 34. The antigen-specific antibodies (Ab1) 46, referred to as capturing antibodies, may be primary or secondary antibodies. The antigen-specific antibodies (Ab1) 46 are bound to the surface of the reaction chamber 34 via adsorption. The surface of the reaction chamber 34 also is coated with magnetic-responsive micro-beads 50 by desiccation. The magnetic-responsive micro-beads may be desiccated on the same region of the device where Ab1 antibodies 46 are bound, or in a region preceding where the Ab1 antibodies 46 are bound. The magnetic-responsive micro-beads are coated with antigen-specific antibodies (Ab2) to form antigen-specific antibody-coated magnetic-responsive micro-beads 50. These antigen-specific antibodies (Ab2) may be primary or secondary antibodies. As the liquid sample flows into the reaction chamber 34 via an assay inlet 36, the antigen-specific antibody-coated magnetic-responsive micro-beads 50 are rehydrated and dispersed in the liquid, and any antigen molecules 48 contained in the sample bind to the antigen-specific antibodies (Ab1) 46 immobilized on the surface of the reaction chamber, and to the antigen-specific antibodies (Ab2) coating the magnetic beads, forming Ab1-antigen-Ab2-coated magnetic-responsive micro-bead complexes 52 (FIG. 8B). The formation of Ab1-antigen-Ab2-coated magnetic-responsive micro-bead complexes 52 anchors the bound antibody-coated magnetic-responsive micro-beads 50 onto the surface of the reaction chamber 34. After all antigen molecules 48 have reacted to form the Ab1-antigen-Ab2-coated magnetic-responsive micro-bead complexes 52, any unbound, i.e., free, antibody-coated magnetic-responsive micro-beads 50 exit the reaction chamber via an assay outlet 38 (FIG. 8C), leaving behind the bound antibody-coated magnetic-responsive micro-beads 50 in the reaction chamber 34. FIG. 9 shows the formation of the Ab1-antigen-Ab2-coated magnetic-responsive micro-bead complex 52 as a liquid sample containing an antigen 48 flows through the reaction chamber 34 and rehydrates the antibody-coated magnetic-responsive micro-beads 50.

A negative liquid sample, i.e., a sample not containing detectable traces of the targeted analyte, results in zero antibody-coated magnetic-responsive micro-beads anchored to the reaction chamber's surface, as the Ab1-antigen-Ab2-coated magnetic-responsive micro-bead complexes cannot form. An analyte (i.e., antigen)-positive sample, on the other hand, results in antibody-coated magnetic-responsive micro-beads anchored to the reaction chamber's surface via the Ab1-antigen-Ab2-coated magnetic micro-bead complexes. Thus, the higher the concentration of analyte in the liquid sample, the greater the number of magnetic-responsive micro-beads anchored to the reaction chamber's surface, and hence the fewer the number of free magnetic-responsive micro-beads reaching the reaction chamber assay outlet. In the extreme case of very high analyte concentration, all antibody-coated magnetic-responsive micro-beads will be anchored to the reaction chamber's surface, and none will exit through the reaction chamber's assay outlet.

After flowing through the reaction chamber, the liquid sample, self-propelled by capillary action, reaches the pScreen™ magnetic bead concentration counter portion of the device (which principle of operation has been described previously). If the liquid sample flowing into the test micro-channel and the calibration micro-channel contains no magnetic-responsive micro-beads, the flow rate in both the test and calibration micro-channels will be identical, and thus the sample volume collected in each of the graduated columns will be identical. The user easily is able to observe that the volume of sample in each of the graduated columns is of equal length. On the other hand, if the sample coming from the micro-channel splitter contains magnetic-responsive micro-beads in any concentration other than zero, the flow of the liquid in the test micro-channel will be retarded (due to the magnetically-induced flocculation of the magnetic micro-beads). Hence, the length of the volume of liquid in the test graduated column will be less than the length of the volume of liquid in the calibration graduated column by an amount proportional to the magnetic-responsive micro-bead concentration in the volume of liquid flowing into the graduated columns. In other words, the higher the magnetic-responsive micro-bead concentration in the liquid reaching the test and calibration micro-channels, the greater the difference in the lengths of the volume of liquid observed in the two graduated columns. The resulting difference between the volumes of liquid collected in the two graduated columns is easily visible to the naked eye.

In an embodiment of the pScreen™ microfluidic immunoassay device, described in detail above and shown in FIG. 4, the test micro-channel (Cm) is split into three test micro-channels 22, 22' and 22" which run parallel to each other. In another embodiment of the pScreen™ microfluidic immunoassay device, described in detail above and shown in FIG. 5, the test micro-channel (Cm) is split into four micro-channels 22 which run parallel to each other.

Figure 10:
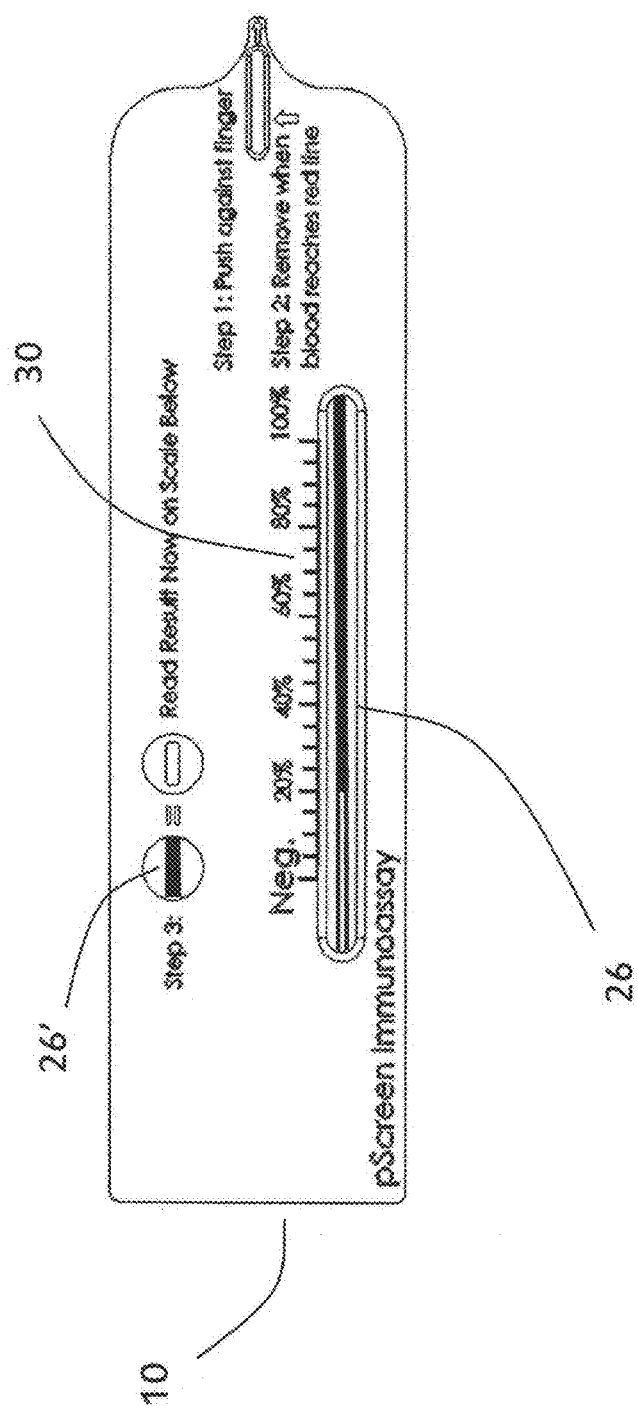
FIG. 10 is an artistic rendering of the pScreen™ immunoassay device, according to the embodiments of the invention.

FIG. 10 shows the pScreen™ microfluidic immunoassay device 10, according to the embodiments of the invention, in which the calibration column is only partially visible. In this embodiment, the read-out is taken when the portion of the calibration column that is visible changes color, i.e., fills up with liquid.

EXAMPLES

The present invention is more particularly described in the following non-limiting examples, which are intended to be illustrative only, as numerous modifications and variations therein will be apparent to those skilled in the art.

Example 1

Scientific Basis and Technology Feasibility of the Present Invention (A) Introduction The data presented herein describe the effect that flocculation of magnetic-responsive micro-beads in a micro-channel has on the flow resistance of liquid in the micro-channel. A liquid seeded with magnetic-responsive micro-beads in a micro-channel that is exposed to a magnetic field gradient produces a localized micro-bead flocculation. This localized micro-bead flocculation results in a localized reduction of the cross section of the micro-channel, and thus in a localized increase of the flow resistance across the flocculation region. The increase in resistance, in turn, results in an increased pressure drop across the flocculation region due to the energy loss in maintaining the flow across the reduced cross-section of the micro-channel. If the external forces responsible for the formation of the micro-bead flocculation are stronger than the flow shear-stress on the micro-beads and their aggregates, the micro-beads' flocculation increases in magnitude as more incoming micro-beads are added. In the case of a constant-pressure driven flow (relevant to the present invention), the increased pressure drop results in a reduction of the micro-channel flow rate. This study investigated and analyzed this phenomenon, and the results are reported below. These experimental results provide the scientific basis upon which the pScreen™ technology and the present invention have been developed.

(B) Experimental Methodology

Experimental data with respect to the effect of magnetic micro-bead flocculation on flow rate in micro-channels are presented. FIG. 1 is an illustration of a constant pressure flow system comprised of two micro-channels. Test micro-channel 22 (Cm) was exposed to a high-magnetic field gradient, while calibration micro-channel 20 (Co) served as a control. The pressure difference driving the flow between the micro-channel inlets 14, 14' and micro-channel outlets 16, 16' was equal between the two micro-channels 20, 22. A liquid sample seeded with a known concentration of magnetic-responsive micro-beads 12 was added to both micro-channels 20, 22 and the flow rate in both micro-channels 20, 22 was recorded over time. Flocculation of the micro-beads was created by means of a localized high-gradient magnetic field generated by two magnets 24, 24'.

Experiments were conducted using micro-channels fabricated from glass capillary tubes having an inner diameter of 50 μm and 100 μm. The length of the capillary tubes was varied between 3.0 cm and 7.5 cm. The magnetic field was generated by two neodymium-iron-boron (NdFeB) permanent magnets 24, 24' (25 mm×6 mm×1.5 mm; maximum surface field: 0.3 T). The magnets 24, 24' were aligned lengthwise along opposite poles. The test micro-channel 22 capillary tube exposed to the magnetic field was placed between the gaps formed between the opposite poles of the NdFeB magnets 24, 24'.

Both micro-channel capillary tubes 20, 22 were partially inserted into a rubber stopper portion of a glass vacutainer tube (not shown), leaving about 0.5 cm of the ends of the capillary tubes visible. Each capillary tube inlet and outlet was inserted in a polystyrene tubing (not shown) having an inner diameter of 360 μm, which tightly fit the 360 μm outer diameter of the two micro-channel capillary tubes 20, 22. One end of the tubing lead directly to a reservoir containing the liquid sample with the magnetic micro-bead solution 12, and the other end of the tubing lead to the vacutainer tubes which collected the fluid exiting the micro-channel outlets 16, 16'. The sample reservoir 12 was open to the air, and thus was at atmosphere pressure. The vacutainer tubes were sealed and kept under a constant vacuum. The pressure difference between the sample reservoir 12 and the vacutainer tubes induced the liquid sample to flow from the reservoir into the vacutainer tubes. The pressure difference was maintained at 0.6 mmHg per cm of capillary tube to provide equal flow rate across capillary tubes of different lengths. Experiments were run in tandem, using two capillary tubes: one for the calibration, i.e., control, micro-channel 20; and one for the test micro-channel 22 exposed to the magnetic field gradient. Both micro-channel capillary tubes 20, 22 were kept at the same differential pressure and drew fluid from the same sample reservoir 12. In the calibration micro-channel capillary tube 20, the sample flowed freely. In the test micro-channel capillary tube 22, the applied magnetic field gradient induced micro-bead flocculation. The calibration and test micro-channels 20, 22 were run simultaneously to eliminate common error, such as variation in atmospheric pressure, changes in viscosity due to fluctuation in temperature, and variations in micro-bead concentration. The suspension medium was 35% (by wt.) glycerol and 65% water to achieve a viscosity similar to that of blood (about 3.6 cP). Green fluorescent dye was added to the suspension medium to increase visibility of the solution exiting the two micro-channel capillary tubes 20, 22. Also added to the medium were smooth carboxyl magnetic micro-beads (Spherotech, Inc.) with a diameter of 4.7 μm or 8.3 μm. Tests were conducted with a micro-bead concentration between 100 micro-beads/μl and $50 \times 10^3$ micro-beads/μl. Sample volumes were between 50 μl to 200 μl and initial flow rates were 0.01 μl/sec. As the sample fluid exited the micro-channel capillary tubes 20, 22, it formed small drops before falling into the vacutainer. The measurement of flow rate was calculated by dividing the drop volume with the time interval between drops. The falling drop rate was recorded with a DVD video camera. Post video analysis provided the flow rate vs. time. Additional experiments were conducted without a vacutainer. The micro-channel outlets 16, 16' were connected to long polystyrene tubing (not shown) which was placed near a graduated ruler. The flow rate was measured by recording the advancement of the fluid meniscus inside the tubing as a function of time. Flow rate values in the glass calibration micro-channel capillary tube 20 not exposed to the magnetic field gradient were compared with theoretical Hagan-Poiseuille flow $Q=(\pi a^4)\Delta P/(8\mu L)$ (wherein a is the tube radius, $\Delta P$ is the pressure difference across the micro-channel, μ is the fluid viscosity, and L is the tube length) for a fully developed laminar flow of a Newtonian fluid in a cylindrical tube. Additional experiments were conducted using a micro-channel configuration as shown in FIG. 2 and fabricated in poly(lactic-co-glycolic acid) (PLGA) and Polyethylene terephthalate by laser etching as above described.

(C) Macroscopic Experimental Results and Data Analysis

Figure 11:
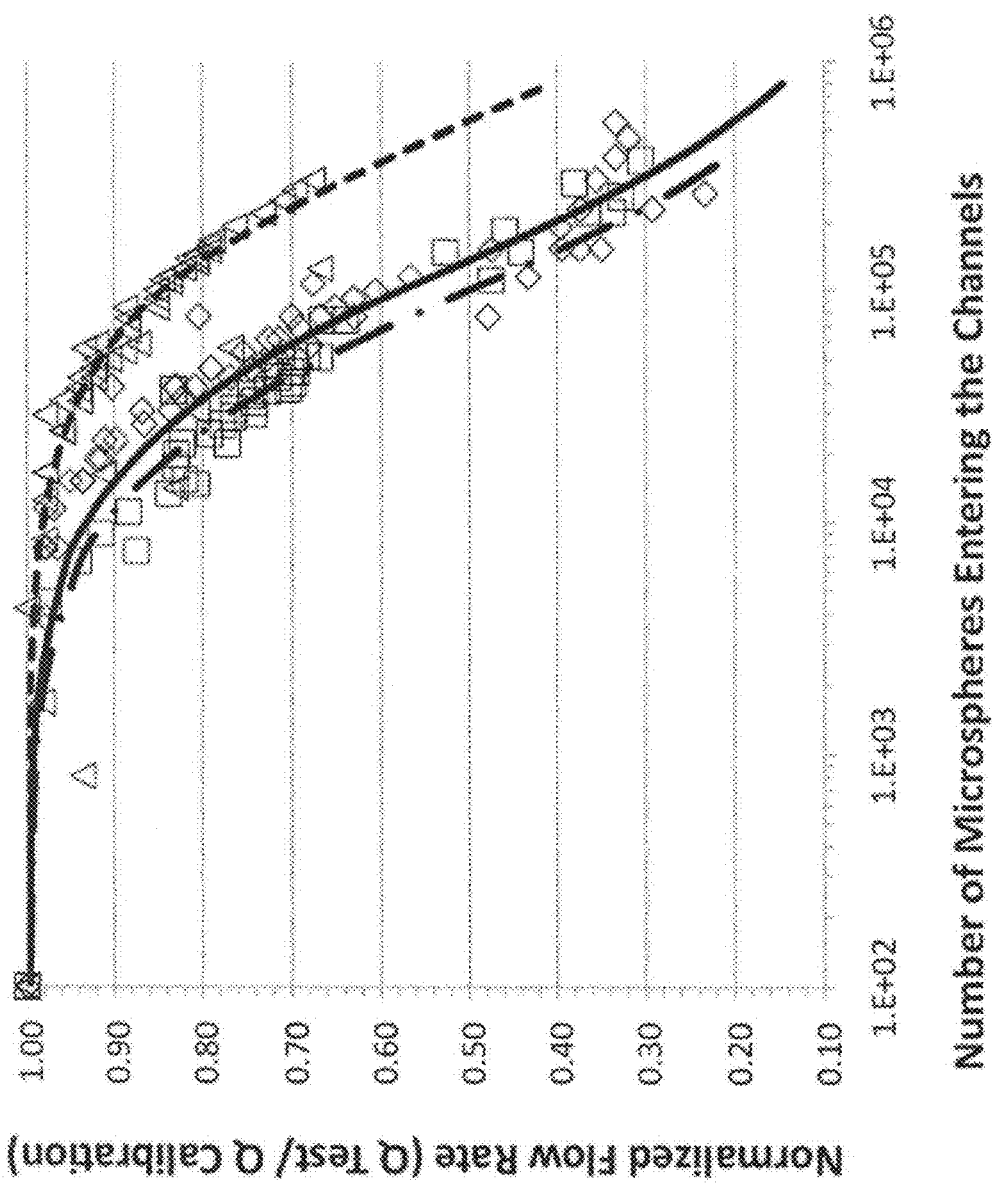
FIG. 11 is a graph showing reduction in fluid flow rate, i.e., the ratio between flow rate in the test (with magnetic field) and calibration (without magnetic field) micro-channels versus the number of magnetic-responsive micro-beads in the flocculation region.
Figure 13:
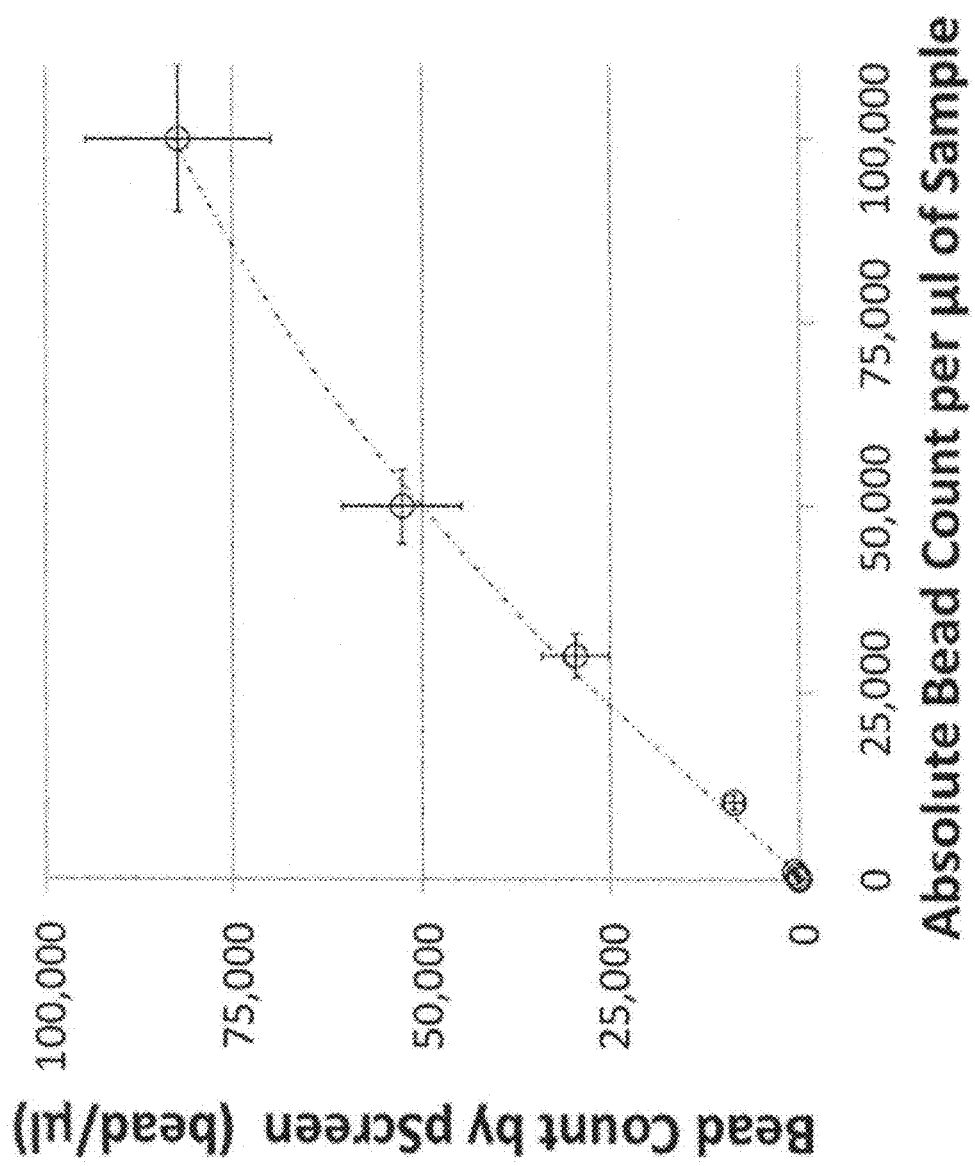
FIG. 13 is a graph showing the concentration of magnetic-responsive micro-beads in a solution obtained using the pScreen™ device versus the nominal concentration as tested by standard hemocytometry.

FIG. 11 shows the normalized flow rate, i.e., the ratio between the flow rate in the test micro-channel capillary tubes (exposed to the magnetic field gradient) and the calibration micro-channel capillary tubes (not exposed to the magnetic field gradient) versus the number of magnetic-responsive micro-beads in the flocculation region. The number of magnetic-responsive micro-beads is given by the product of the flow rate times the magnetic-responsive micro-bead concentration in the sample. The data show that the normalized flow rate is a monotonic function of the number (over three orders of magnitude) of magnetic-responsive micro-beads in the flocculation region. The amount by which the flow rate is reduced due to the pressure drop caused by the flocculation depends on the overall capillary length and the size of the flocculation zone. Thus, different aspect ratios of magnetic field length along the micro-channels versus the total length of the micro-channels also were investigated. FIG. 13 shows three data curves for different aspect ratios of magnetic field (concentrator) length versus the total length of the micro-channels [ratios range from 0.17 (triangle) to 0.24 (diamond) to 0.4 (square)]. To the investigators' knowledge, these data are the first to provide direct measurements of the effect of magnetic-responsive micro-bead flocculation on fluid flow rate in micro-channels.

(D) Data Analysis

These experimental data demonstrate that over a wide range the normalized flow rate, Qm/Qo, is a monotonic function of the number of magnetic-responsive micro-beads entering the capillary tubes. What is presented herein is a phenomenological model based on the Poiseuille equation that the investigators derived to corroborate these results. The model relates the flow rate to the reduction in micro-channel cross-section due to the formation of flocculation. The model predicts the following relationship between flow rate and number of magnetic-responsive micro-beads:

$$\hat{Q} = 1/(1 + \alpha N), \quad \text{Equation (9)}$$

where $\alpha$ is a parameter defined below:

$$\alpha = [(a/R_{\it{eff}})^4 - 1]/LB, \quad \text{Equation (10)}$$

$$B = \frac{3}{4}(1 - \varepsilon)(a^2 - R_{\it{eff}}^2)/r^3 \quad \text{Equation (11)}$$

where $\hat{Q}$ is the normalized flow rate, defined as Qm/Qo, N is the number of micro-beads in the flocculation, a is the capillary tube radius, $R_{\it{eff}}$ is the lumen length of the capillary tube not blocked by micro-bead flocculation, L is the capillary tube length, r the radius of the micro-beads, $\varepsilon$ is the porosity of the micro-bead flocculation in the test micro-channel, and B is a constant that is introduced to collected different terms under a single parameter for adding simplicity and clarity to the equation form. The model predicts with high accuracy (solid lines, FIG. 11) the curve shift with changes in capillary length over magnetic field region lengths. This model provided analytical guidance for designing the specifications of the device of the present invention.

(E) Microscopic Experimental Results

Figure 12:
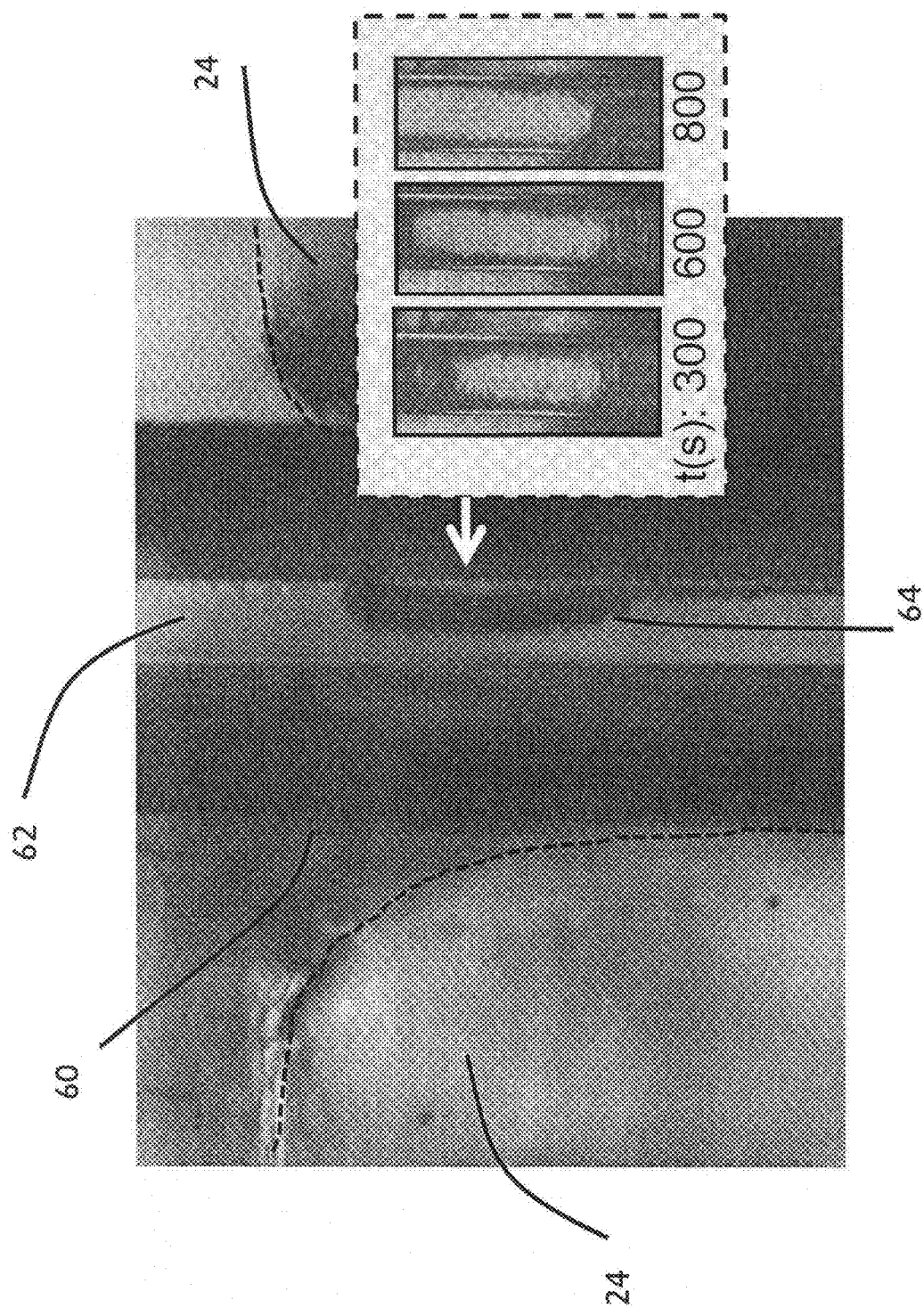
FIG. 12 is a photomicrograph showing magnetically-induced flocculation of magnetic-responsive micro-beads at a concentration of about 2,000 micro-beads/µl in a test micro-channel, according to the embodiments of the invention; the inset shows the variation in flocculation at 300 seconds, 600 seconds and 800 seconds.

In order to observe the mechanism of magnetically-induced flocculation, microscopic studies were performed using an inverted microscope (Olympus, IX70, 20× magnification). This phenomenon was visualized using a solution seeded with RBC-sized magnetic-responsive micro-beads, having a diameter of 4 μm or 8 μm, in capillary tubes having a diameter of 50 μm or 100 μm. FIG. 12 shows an example of flocculation formed in a 2,000 micro-beads/μl analog solution. Flocculation initially formed at the leading edge of the magnet (corresponding to the greatest magnetic field gradient.) The size of the flocculation grew over the entire length of the magnetic field region. When the size of the flocculation covered the length of the magnetic field region, the flocculation behaved as a fluidized bed. Magnetic-responsive micro-beads downstream were released, while upstream incoming magnetic-responsive micro-beads were added to the flocculation.

Example 2 pScreen™ Prototype Fabrication and Testing (A) Fabrication

Two sets of pScreen™ prototypes were fabricated: (1) a bench top prototype with multiple micro-channels for simultaneous testing of various samples; and (2) a single-use, portable, lab-on-card device. The pScreen™ bench-top prototype was described in the previous section. The pScreen™ lab-on-card prototype was realized using standard microfluidics fabrication techniques. In brief, the micro-channels were etched using a laser etcher system on a poly(ethylene terephthalate) glycol (Petg) substrate. The channels then were sealed using a matching poly(lactic-co-glycolic acid) (PLGA) top by thermal bonding using a hot press. The magnetic field gradient was obtained by placing two small magnets in an N—S configuration underneath the test channel. The pScreen™ lab-on-card prototype also was fabricated using injection cast molding in which the prototype was fabricated in poly(methyl methacrylate) (PMMA).

(B) Experimental Data for a Microfluidic Device for Detecting and Quantifying the Concentration of Magnetic Micro-Beads Two pScreen™ prototypes were tested using a variety of fluids such as, without limitation, blood, blood-analogs, or PBS buffer solution with different concentrations of surfactant. Tests were conducted using magnetic-responsive micro beads having a diameter of 4.1 μm or 8 μm. Sample concentrations between 100 micro-beads/μl and 200,000 micro-beads/μl were used. The concentration of magnetic-responsive micro-beads was determined by recording the level of the fluid on the calibration and test graduated column scales. Each mark on the scale corresponded to a given amount of fluid volume which flowed through the micro-channels. The relationship derived in Equation 8 was applied to convert the recorded volumes in magnetic-responsive micro-bead concentration. The analytic expression of the relationship between the volumes Vo and Vm, specific for the tested prototypes, was derived by computing Equations (5) through (8), with $\hat{Q}$ given in Equations (9) through (11). To be especially noted is the fact that all of the equations provided above do not include time as a variable. Hence, it is not necessary to monitor/read the device's result at any specific time. The device reading at any time provides the same read-out. FIG. 13 is a graph showing magnetic-responsive micro-bead concentration measured using the pScreen™ device (y-axis) of the present invention versus magnetic-responsive micro-bead concentration measured with a standard hemocytometer (x-axis).

(C) Experimental Data for a pScreen™ Immunoassay

Figure 14:
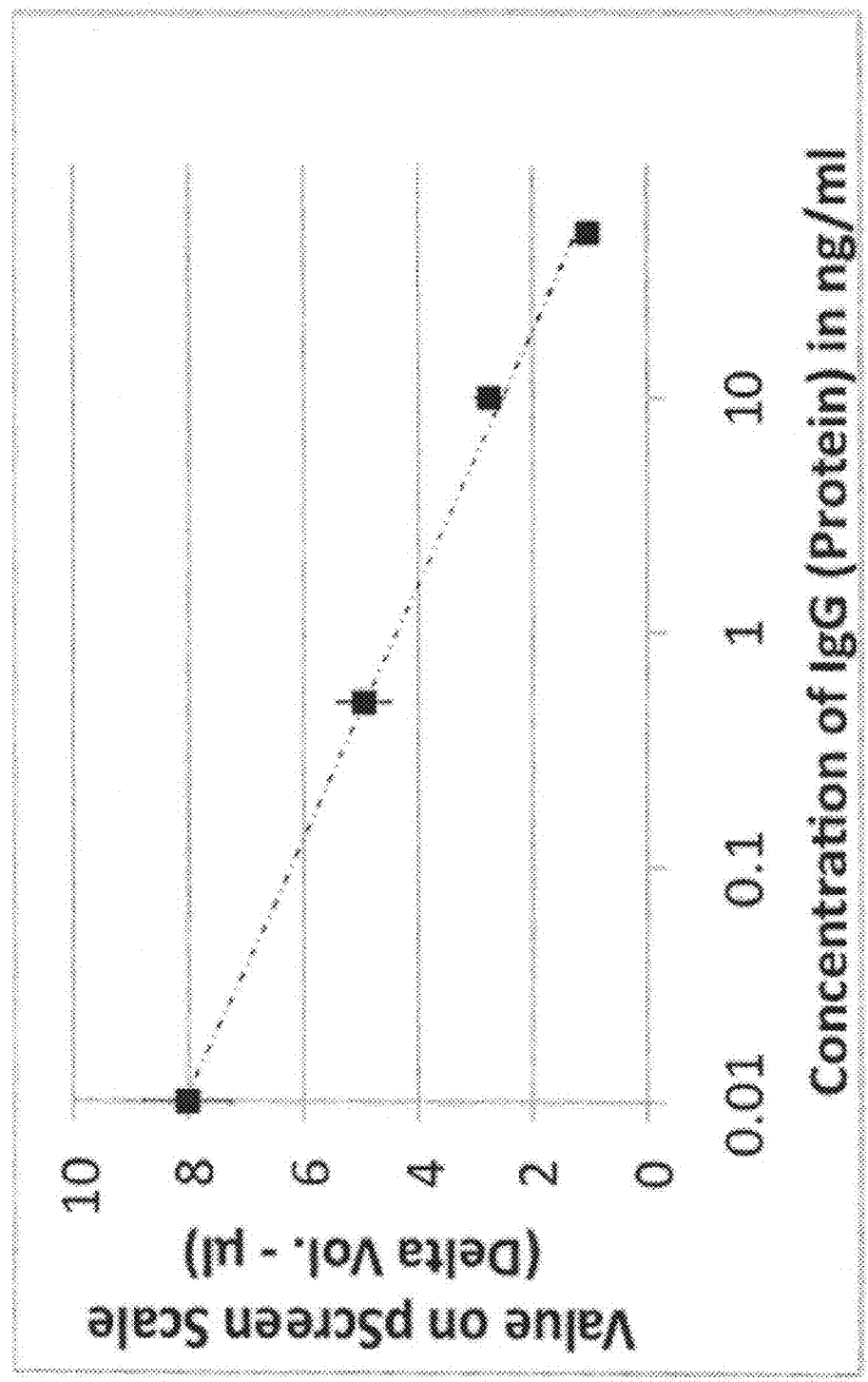
FIG. 14 is a graph showing the concentration of immunoglobulin (IgG) in a solution obtained using the pScreen™ immunoassay.

Several pScreen™ immunoassay prototypes were tested using buffer solutions containing various concentrations of mouse-IgG antibody prepared by titration from a known concentration IgG standard. The concentration of mouse-IgG antibody ranged from 0.5 ng/ml to 100 ng/ml. Tests were conducted using magnetic-responsive micro-beads coated with anti-mouse IgG antibody and coating the surface of a reaction chamber with anti-mouse IgG antibody. Sample volume ranged from 30 μl to 60 μl. The IgG antibody concentration was determined by recording the level of the fluid on the calibration and test graduated column scales. Each mark on the scale corresponded to a given amount of fluid volume which flowed through the micro-channels. FIG. 14 is a graph showing the difference between the volume collected in the control column (Vo) and the volume collected in the test column (Vm) (y-axis) versus the known concentration of IgG antibody (x-axis).

Examples 3 to 6 provide guidance regarding the detection and quantification of magnetic-responsive micro-beads and amount of analyte in a liquid sample. Also provided are examples showing how to obtain a set of calibration curves for any embodiment by means of the claimed proxies herein, i.e., between the ratio Qm/Qo, the difference Qo−Qm, and the ratio $(Qo-Qm)^p/(Qm)^q$, and the number of magnetic-responsive micro-beads and the concentration of analyte in a fluid. The examples provided show how to derive Equation 8 for any specific embodiment and provide working examples for a selected embodiment. Equation 8 is a direct result of the claimed proxy between the ratio Qm/Qo and the number of magnetic-responsive micro-beads. Equation 8 converts the volume of liquid sample passing through the control micro-channel, Vo, and through the test micro-channel, Vm, into the magnetic-responsive micro-bead concentration and the analyte concentration in a liquid sample.

Example 3

Proxy Relationships Between Flow Rate and Micro-Bead Concentration

The present invention provides a method of detecting and quantifying the concentration of magnetic-responsive micro-beads in a liquid sample, by calculating the ratio Qm/Qo, the difference Qo−Qm, and the ratio $(Qo-Qm)^p/(Qm)^q$, wherein p and q are derived through a calibration process, wherein the ratios Qm/Qo and $(Qo-Qm)^p/(Qm)^q$ are a proxy for the number of magnetic-responsive micro-beads in the liquid sample, and then quantifying the concentration of magnetic-responsive micro-beads in the liquid sample.

Three methods are provided to show how to use these proxy relationships and how to derive in practice the number of magnetic-responsive micro-beads in a liquid sample. The first method analytically derives these relationships from the physical dimensions of a specific embodiment. The second method provides a calibration process that enables the calibration of any embodiment. The third method teaches how to use the volume of sample passing through the control micro-channel, Vo, and through the test micro-channel, Vm, to derive the concentration of magnetic-responsive micro-beads.

Method 1. Relationship Between Normalized Flow Rate, Qm/Qo, and Number of Micro-Beads The relationship between the normalized flow rate, Qm/Qo, and the number of micro-beads entering the capillary tubes (i.e., micro-channels) is analytically derived for a specific embodiment having the following dimensions and values:

Test micro-channel and calibration (control) micro-channel: each with a circular cross-section with a radius of 50 μm; and a length of 15 mm.

Micro-beads: radius of 2 μm
Porosity of the flocculation: 0.55
Pressure difference between the inlet and outlet of both micro-channels: maintained constant at about 1 mmHg per cm.

The flow rate in the control micro-channel, Qo, is described by the Hagen-Poiseuille equation, and is equal to:

$$Q_o = \Delta P/R_o, \text{ with: } R_o = 8\mu L/(\pi a^4),\quad \text{Equation (12)}$$

where ΔP is the pressure drop across both micro-channels; Ro is the micro-channel's flow resistance; μ is the liquid sample viscosity; a is the micro-channel's radius, and L is the micro-channel's length.

The flow rate in the test micro-channel, Qm, is given by:

$$Q_m = \Delta P/R_m, \text{ with: } R_m = 8\mu(L-\lambda)/(\pi a^4) + \mu\lambda/(\pi a^2 k),\quad \text{Equation (13)}$$

where λ is longitudinal section of the length of the test micro-channel occupied by the micro-bead flocculation; L−λ is the remaining length of the micro-channel flocculation-free; and k is the Darcy's constant. The first term in Equation 13 is the Hagen-Poiseuille equation for the flocculation-free section of the test micro-channel, and the second term is Darcy's law for the section of the test micro-channel occupied by the micro-bead flocculation. Darcy's law is known by those skilled in the art to accurately describe flow of fluid through packed beads and bead flocculation. In this example, the Reynolds' number is low (<2) (Reynolds' number depends on an embodiment's physical dimensions and flow rates, and is a well know parameter that describes the physical properties of fluid in a flow), and thus the Darcy's constant takes the known form:

$$k = r^2 \epsilon^3/(15(1-\epsilon)^2),\quad \text{Equation (14)}$$

where ε is the porosity of the micro-bead flocculation in the test micro-channel, i.e., the fraction of volume of the test micro-channel not occupied by the micro-beads; and r is the micro-bead's radius.

Taking the ratio of Equation 13 over Equation 12, one gets:

$$Q_m/Q_o = R_o/R_m = \frac{8\mu L}{\pi a^4} \Big/ [8\mu(L-\lambda)/(\pi a^4) + \mu\lambda/(\pi a^2 k)]$$

By rearranging the terms in the above equation, one gets:

$$Q_m/Q_o = 1/[1+(\lambda/8L)\cdot(a^2/k-1)].\quad \text{Equation (15)}$$

It is noted that Equation 15 does not contain liquid sample viscosity.

The longitudinal section of the length of the test micro-channel occupied by the micro-bead flocculation, λ, increases with the number of micro-beads, N, that have entered the test micro-channel and formed the flocculation under the effect of the magnetic field. These quantities, λ and N, thus are related by the following identity:

$$\lambda = N/\hat{B}, \text{ with: } \hat{B} \equiv \frac{3}{4}a^2(1-\varepsilon)/r^3 \quad \text{Equation (16)}$$

where $\hat{B}$ is a constant that is introduced to collect different terms under a single parameter for adding simplicity and clarity to the equation.

By putting Equation 16 into Equation 15, one gets:

$$Q_m/Q_o = 1/[1+(N/8L\hat{B})(a^2/k-1)]\quad \text{Equation (17)}$$

or alternatively, $$Q_m/Q_o = 1/[1+\hat{\alpha}N], \text{ where: } \alpha = (1/8L\hat{B})(a^2/k-1)$$

Equation 17 provides the relationship that enables the measurement of the number of micro-beads by measuring the ratio Qm/Qo. Thus, in this example, Equation 17 becomes:

$$Q_m/Q_o = 1/[1+2.63\times 10^{-6}\cdot N],\quad \text{Equation (18)}$$

In this example, Equation 18 is used as follows:

Given a fluid sample of unknown micro-bead concentration, for which the concentration needs to be determined, the operator first runs the sample through the micro-channels as described above and measures periodically the flow-rates, Qm and Qo. The measurements can be done at any time while the liquid sample is flowing into the micro-channels. Then, by putting the ratio, Qm/Qo, obtained from each measurement into Equation 18, the operator gets the number of micro-beads that have entered the test micro-channel, N, at the time the flow rate measurements have been taken. To compute the micro-bead concentration, the operator divides the value of N by the total volume of fluid that passed through the test micro-channel at the time flow rate measurements have been taken, which also is equal to the sum of the products of the test micro-channel flow rates by the length of the time interval between measurements. The shorter the time interval between measurements, the more precise is the obtained value of the number of micro-beads and of the micro-bead concentration. Table 1 provides the values obtained in this example:

TABLE 1

| Time (second) | Qo µl/sec | Qm µl/sec | Qo/Qm | N | Vm (µl) | Concentration (beads/µl) |
|---|---|---|---|---|---|---|
| 54 | 0.01 | 0.0100 | 1.000 | 0.0E+00 | 8.5 | 0.0E+00 |
| 906 | 0.01 | 0.0094 | 0.940 | 4.0E+04 | 17.1 | 2.3E+03 |
| 1818 | 0.01 | 0.0093 | 0.934 | 4.4E+04 | 26.1 | 1.7E+03 |
| 2778 | 0.01 | 0.0089 | 0.888 | 7.9E+04 | 35.0 | 2.3E+03 |
| 3786 | 0.01 | 0.0085 | 0.845 | 1.1E+05 | 43.8 | 2.6E+03 |
| 4830 | 0.01 | 0.0082 | 0.816 | 1.4E+05 | 52.6 | 2.7E+03 |
| 5910 | 0.01 | 0.0079 | 0.789 | 1.7E+05 | 61.4 | 2.7E+03 |
| 7026 | 0.01 | 0.0076 | 0.763 | 1.9E+05 | 70.3 | 2.8E+03 |
| 8190 | 0.01 | 0.0073 | 0.732 | 2.3E+05 | 79.1 | 2.9E+03 |
| 9390 | 0.01 | 0.0071 | 0.710 | 2.6E+05 | 87.8 | 2.9E+03 |
| 10614 | 0.01 | 0.0070 | 0.696 | 2.7E+05 | 96.6 | 2.8E+03 |

Table 1 shows the time in seconds at which each measurement was taken; the experimental measurements of the flow rate, Qo, in µl/second in the control micro-channel; and the flow rate, Qm, in µl/second in the test micro-channel. (For the method to work, it is not important how the flow rates, Qo and Qm, are measured. For example, the flow rates can be measured by using commercially available flow meters placed in series with the micro-channels, or as described in detail above in Example 1. The ratio, Qm/Qo, then is computed and shown in the table's fourth column, from which the number of micro-beads, N, is derived using Equation 18 and shown in the table's fifth column. The volume, Vm, is calculated by taking the sum of the products of the test micro-channel flow rates by the length of the time interval between measurements, and is shown in the table's sixth column (alternatively, the volume, Vm, also can be measured as an independent variable, as described above). Then, micro-bead concentration is derived by dividing the N column by the Vm column, with the result shown in the table's seventh column. It is noted that the concentration slightly varies between measurements, and thus to obtain a more precise value, the average of these measurements may be taken. In this example, the micro-bead concentration is equal to 2,570 micro-beads/µl of liquid sample.

Equation 18 provided herein was derived for this specific embodiment. A person skilled in the art, however, would understand that following the same process, the relationship between the normalized flow rate and the number of micro-beads entering the test micro-channel can be derived for other embodiments by putting the appropriate value of the Darcy's constant in Equation 15. The Darcy's constant is well known by those skilled in the art to depend on the micro-channels' shape, geometry, physical dimensions, design, flow rates, as well as an embodiment's Reynolds number. By using the appropriate Darcy's constant, the invention may be practiced for other embodiments having, for example, non-cylindrical micro-channels and/or non-spherical micro-beads, and/or non-uniformly-sized micro-beads.

In addition, for other embodiments, in which micro-bead flocculation does not occupy the entire test micro-channel's cross-section, but only occupies outer layers, the relationship between the normalized flow rate, Qm/Qo, and the number of micro-beads entering the capillary tubes is given in Equations 9 to 11.

Method 2. Calibration Process

Provided herein is the construction of a set of calibration curves which provide the relationship between the normalized flow rate, Qm/Qo, and the number of micro-beads entering the test micro-channels. The method described herein allows one to avoid the need to use complex analytical expressions, which for some embodiments may be too complex to be represented in a mathematical closed form such as Equation 18.

For a given embodiment, the calibration process involves running a liquid solution containing a known concentration (the calibration solution) of magnetic-responsive micro-beads through the control and test micro-channels, as shown in FIGS. 1 and 4. The flow rates, Qm and Qo, then are measured at different time intervals and recorded, and the total volume passing through the test micro-channel also is recorded, as described above. The shorter the time interval between recordings, the more precise is the resulting calibration curve. For each value of flow rate recorded, the number of micro-beads that have entered the test micro-channel and added to the flocculation is computed by taking the product between the volume, Vm, passing through the test micro-channel and the value of the known concentration of the micro-beads. Then, the ratio, Qm/Qo, for each measurement is plotted versus the number of micro-beads computed, as previously described. The process may be repeated multiple times using calibration solutions with different known values of micro-bead concentration; the more times this process is repeated, the more precise are the calibration curves. An example of these plots is shown in FIG. 11 for the embodiment described in the Example 1. Using this calibration curve, micro-bead number in any tested fluid of unknown concentration can be determined from the observed ratio, Qm/Qo, by reading the horizontal value (the micro-bead number) on the calibration curve corresponding with the vertical value (the observed ratio, Qm/Qo) observed during the measurement. The concentration of the calibration solutions are prepared to approximate the expected range of concentration of the liquid samples to be tested.

The same process can be repeated to derive calibration curves that relate the ratio, $(Qo-Qm)^p/(Qm)^q$, with micro-bead concentration in a liquid sample. In this case, the parameters, p and q, are obtained as followed. A solution containing a known concentration of micro-beads and of known volume is passed through the micro-channels and the flow rates, Qm and Qo, are measured. Then, an identical solution is passed through the micro-channels but with a higher flow rate, Qo. This process is repeated at least three times, with flow rates, Qo, which cover the range of flow rates, Qo, for which the embodiment is expected to be used. Then, $(Qo-Qm)^p/(Qm)^q$, with p and q set equal to 1, are plotted for each solution versus the number of micro-beads entering the test micro-channel (determined as previously described) to obtain a set of calibration curves. Then, p and q are independently varied until each curve $(Q_o-Q_m)^p/(Q_m)^q$ collapses on each other to form a single curve. A method to optimize p and q is to solve the following set of equations.

$$[(Q_o-Q_m)^p/Q_m^p]_N^1 = [(Q_o-Q_m)^p/Q_m^p]_N^2$$

$$[(Q_o-Q_m)^p/Q_m^p]_N^1 = [(Q_o-Q_m)^p/Q_m^p]_N^3$$

where the superscript numbers 1, 2, and 3 refers to the calibration curve number, and the subscript N indicates that the values of Qo and Qm in the square brackets are taken when the number of micro-beads entering the test micro-channel is equal to N. The value of N can be chosen arbitrarily, and the process may be repeated for different N values to obtain a more accurate value of p and q across the entire range of numbers of micro-beads.

Method 3. Conversion from Volume to Micro-Bead Concentration—Equation 8 Working Example Provided herein are two processes which may be used for any embodiment in order to convert the volume of sample passing through the control micro-channel, Vo, and the test micro-channel, Vm, into magnetic-responsive micro-bead concentration and concentration of analyte in a liquid sample. The first process analytically derives these relationships from the physical dimensions of the embodiment. The second process provides a calibration method that enables calibration of any embodiment and shows the use of the embodiment in practice.

Process A

Provided is a working example showing how Equations 5 through 8 enable one to derive the concentration of micro-beads in a liquid from the ratio Qo/Qm, using the same dimensions provided above in Method 1 (spherical micro-beads with a radius of 2 μm, micro-channels having a length of 15 mm and a radius of 50 μm, and Qo equal to 0.0 μl/second), and for which the ratio, Qm/Qo, versus the number of micro-beads is provided by Equation 18. By putting Equation 18 into Equation 5, one gets:

$$N_0 = \int_0^{Nm} \frac{dN'}{(1/(1+(2.63\times 10^{-6})\cdot N'))} \qquad \text{Equation (19)}$$

where No is the number of magnetic responsive micro-beads that are passing through the control micro-channel, Nm is the number of magnetic responsive micro-beads that are passing through the test micro-channel, and the prime symbol inside the integral, N', indicates, according to standard convention, that the integral operation is computed on an N variable. Equation 19 is the specific example, for a specific embodiment, of generic Equation 6. By solving the integral, one gets:

$$N_o = N_m + \frac{2.63\times 10^{-6}}{2}(N_m)^2 \qquad \text{Equation (20)}$$

Since No is equal to the product of the magnetic responsive micro-bead concentration, p, times the volume of sample passing through the control micro-channel, Vo; and since Nm is equal to the product of the magnetic responsive micro-bead concentration, ρ, times the volume of sample passing through the test micro-channel, Vm, Equation 20 can be rewritten as:

$$V_o\rho = V_m\rho + \frac{2.63\times 10^{-6}}{2}(\rho V_m)^2; \qquad \text{Equation (21)}$$

$$\text{or}: V_o - V_m = \frac{2.63\times 10^{-6}}{2}(V_m)^2\rho$$

Equation 21 can easily be rearranged as follows:

$$\rho = (V_0 - V_m)\bigg/\left(\frac{2.63\times 10^{-6}}{2}V_m^2\right) \qquad \text{Equation (22)}$$

Equation 22 provides a simple expression that can be used to derive the concentration of micro-beads for any liquid sample with unknown concentration of micro-beads from the measurements of the volumes, Vo and Vm, in this working example. In other words, Equation 22 is a specific example of generic Equation 8. For example, a liquid sample containing an unknown concentration of magnetic-responsive micro-beads is run through the control and test micro-channels, as described above. To obtain the value of this unknown concentration, the volume of the fluid passing through the control micro-channel, Vo, and the volume of fluid passing through the test micro-channel, Vm, are recorded, as described above. Then these values, Vo and Vm, are put into Equation 22 to derive the concentration of magnetic-responsive micro-beads.

Process B

Figure 15:
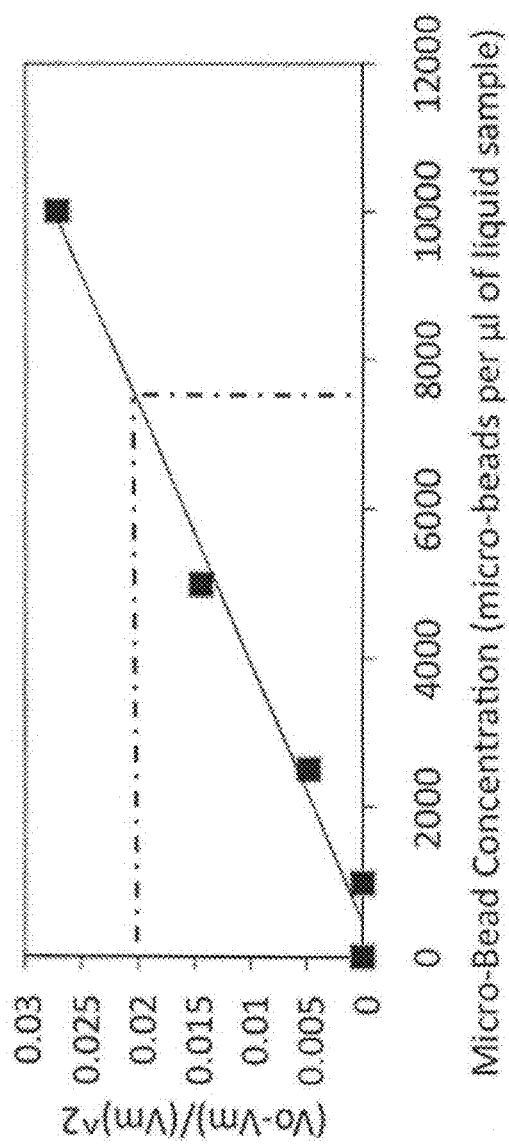
FIG. 15 is a graph showing a calibration curve describing the relationship between $(Vo-Vm)/(Vm)^2$ and the concentration of magnetic-responsive micro-beads, according to the embodiments of the invention.

Provided herein is an example showing how to construct calibration curves for the relationship between volumes, Vo and Vm, and concentration of micro-beads. The process allows one to avoid the need to use complex analytical expressions, which for some embodiments may be too complex to be represented in a simple closed form such as Equation 22. For a given embodiment, a series of solutions of known volume and containing known concentrations of magnetic-responsive micro-beads are passed through the control and test micro-channels, as described above. The concentrations of these test (calibration) solutions are chosen to span the entire range of micro-bead concentrations in the samples to be tested. The volumes, Vo and Vm, then are measured. For the lab-on-card microfluidic pScreen™ magnetic-responsive micro-bead concentration counter embodiment, the volumes, Vm and Vo, can be measured by reading the scale on the control column (Co) and the test column (Cm). Once Vm and Vo have been recorded for all solutions, the ratios, (Vo−Vm)/(Vm)², are plotted as a function of micro-bead concentration. This plot provides a calibration curve that enables the invention to be reduced to practice. Using this calibration curve, the micro-bead concentration of an unknown fluid can be determined from the observed difference, ratio (Vo−Vm)/(Vm)², by reading the horizontal value (micro-bead concentration) on the calibration curve corresponding with the y value (Vo−Vm)/(Vm)² observed during the test, as shown in FIG. 15. For example, as shown in FIG. 15, if the measurement of Vm and Vo for a solution with an unknown micro-bead concentration gives a ratio of (Vo−Vm)/(Vm)² equal to 0.02, then the micro-bead concentration would be 7500 micro-beads/μl. The calibration curve shown in FIG. 15 was obtained using the embodiment shown in FIG. 2, in which the micro-channels' radii is 46 μm, the length of the micro-channels is 15 mm, and the radius of the micro-beads is 2.35 μm.

Example 4

Proxy Relationships Between Flow Rate and Concentration of Analyte in a Liquid Sample

The present invention provides a method of detecting and quantifying the concentration of magnetic-responsive micro-beads in a liquid sample, by calculating the ratio $Q_m/Q_o$, the difference $Q_o-Q_m$, and the ratio $(Q_o-Q_m)^p/(Q_m)^q$, wherein the ratios $Q_m/Q_o$ and $(Q_o-Q_m)^p/(Q_m)^q$ are a proxy for the number of magnetic-responsive micro-beads in the liquid sample, which is a proxy for the concentration of analyte in the liquid sample, and then quantifying the concentration of analyte in the liquid sample, as described below.

As described above, the concentration of magnetic-responsive micro-beads exiting the reaction chamber and entering the two micro-channels is proportional to the concentration of the analyte in the liquid sample. As described herein, the concentrations of these micro-beads are detectable and quantifiable by either using the ratio $Q_m/Q_o$ or the values $V_o$ and $V_m$. Thus, in order to derive the concentration of analyte in a liquid sample, the relationship between the concentration of analyte and the concentration of micro-beads exiting the reaction chamber needs to be calibrated. Two methods are provided, as follows:

Method 1

Figure 8:
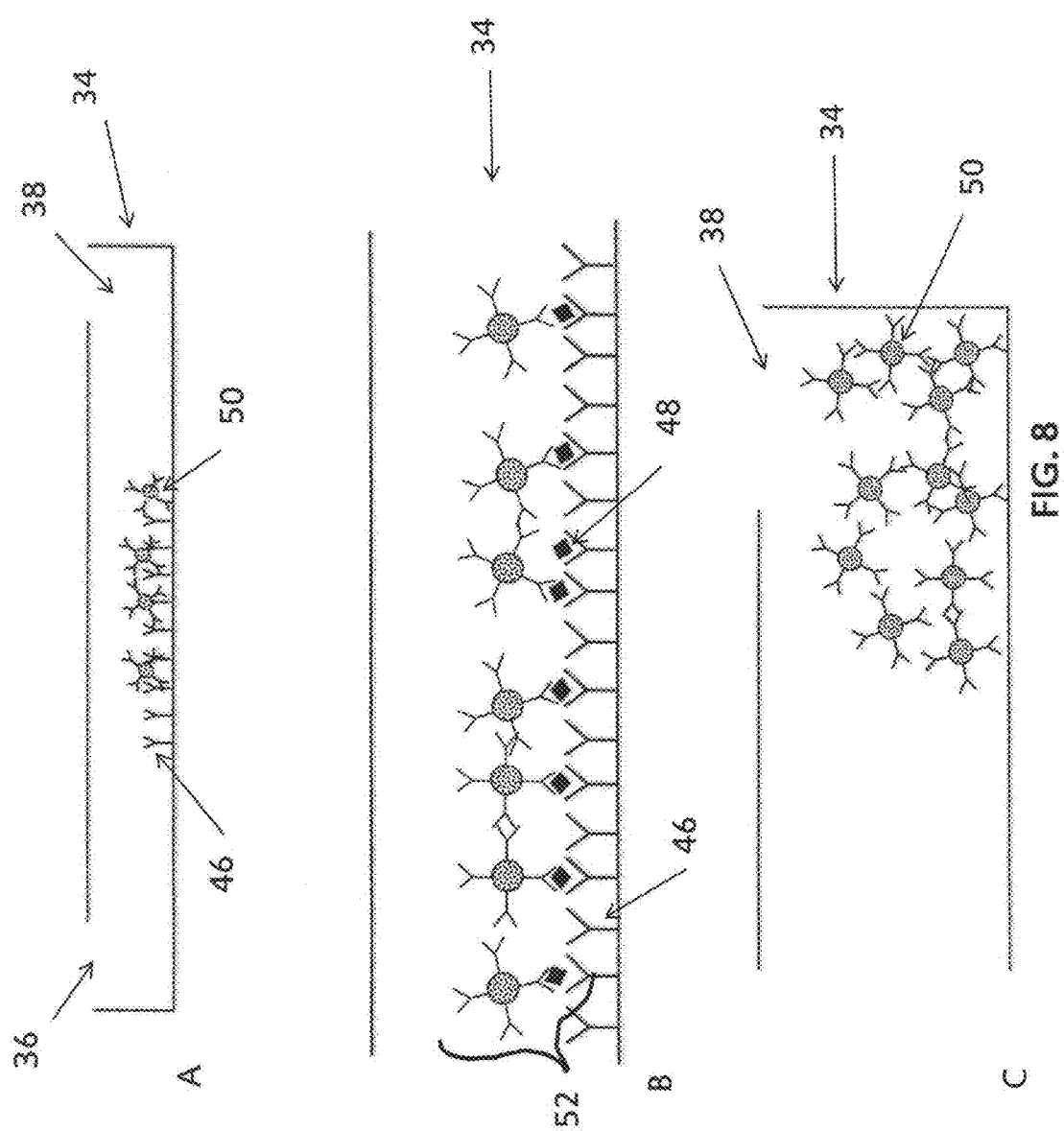
FIG. 8 is a schematic illustration of three different views of a reaction chamber of the pScreen™ immunoassay device, in which (A) shows the secondary antibody (Ab2)-coated magnetic-responsive micro-beads and primary antibody (Ab1)-capturing antibodies on the surface of the reaction chamber; (B) shows the Ab1-antigen-Ab2-magnetic-responsive micro-bead complexes immobilized on the surface of the chamber; and (C) shows unbound, i.e., free, Ab2-magnetic-responsive micro-beads reaching the assay outlet of the reaction chamber, according to the embodiments of the invention.
Figure 9:
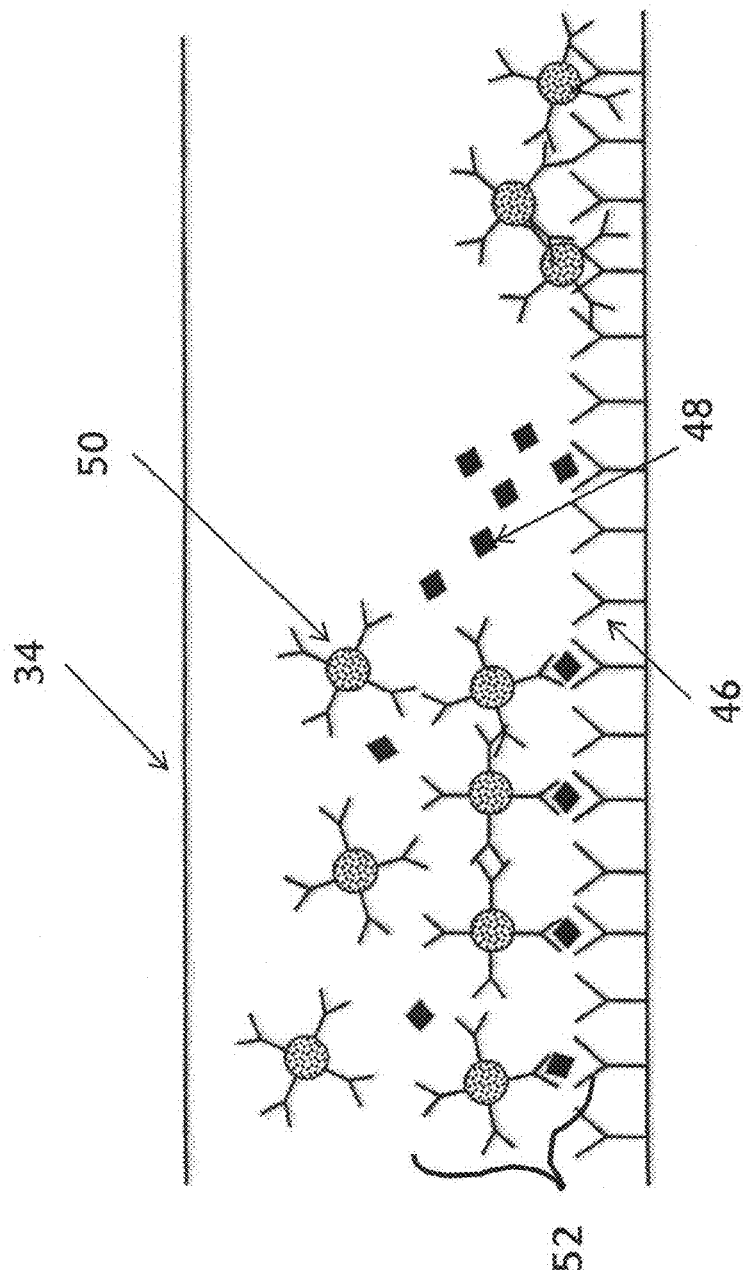
FIG. 9 is a schematic illustration which shows the formation of the Ab1-antigen-Ab2-magnetic-responsive micro-bead complexes as the sample with the antigen flows through the reaction chamber and rehydrates the magnetic-responsive micro-beads, according to the embodiments of the invention.

The first method consists of running a sample with a known concentration of analyte through the reaction chamber and then counting the number of micro-beads binding to the reaction chamber's surface, as shown in FIGS. 8 and 9. The number of micro-beads exiting the reaction chamber is equal to the total number of micro-beads deposited in the reaction chamber (as described above) minus the number of micro-beads binding to the reaction chamber's surface. The process is repeated multiple times using a series of calibration samples obtained from the initial sample by titration. Then the concentration of micro-beads exiting the reaction chamber obtained for each calibration test is plotted as a function of the analyte concentration. In practice, the sample with unknown concentration of analyte is processed as described above and schematically shown in FIGS. 1 and 7. The concentration of micro-beads entering the micro-channels, i.e., the concentration of micro-beads exiting the reaction chamber, is derived as described above. Then, using the calibration curve derived and described above, the concentration of micro-beads is converted into the concentration of analyte.

Method 2

The second method enables the user to derive the calibration curve for any embodiment without counting the number of micro-beads binding to the reaction chamber's surface. To calibrate for any embodiment, a series of solutions of known volume, containing known concentrations of target analyte, are run through the device as described above. The concentrations of these test (calibration) solutions are chosen to span the entire range of expected analyte concentrations of the sample to be tested. The difference, $V_o-V_m$, between the control micro-channel volume, $V_o$, and the test micro-channel volume, $V_m$, is measured for each tested calibration sample and plotted as a function of the calibration sample's analyte concentration. Using this plot (calibration curve), the target analyte in any tested fluid can be determined from the observed difference in volume, $V_o-V_m$, by reading the horizontal value (analyte concentration) on the calibration curve corresponding with the vertical value (the $V_o-V_m$ difference) observed in the test.

Example 5

Working Example—Quantification of Concentration of Micro-Beads in a Liquid Sample

Quantification of the concentration of micro-beads in a liquid sample is performed by using the pScreen™ immunoassay shown in FIG. 2, and having the dimensions as described above in Method 3, Process A. To measure the concentration of micro-beads, the user performs the following steps:

Step 1: Take 50 µl of sample solution and place it on the device inlet.
Step 2: Wait for the sample to flow into the device columns, typically less than 20 minutes.
Step 3: Read the values of the fluid volumes, $V_o$ and $V_m$, filling up each column using the scale on the side of the column
Step 4: Compute the ratio $(V_o-V_m)/(V_m)^2$.
Step 5: The concentration of micro-beads is equal to ratio $(V_o-V_m)/(V_m)^2$ divided by $1.3\times10^{-6}$.

Example 6

Working Example—Quantification of Analyte Concentration in a Liquid Sample

Quantification of the concentration of an analyte in a liquid sample is performed by using the pScreen™ immunoassay shown in FIG. 3, and the calibration curve shown in FIG. 15. To measure the concentration of the analyte, the user performs the following steps:

Step 1: Take 50 µl of sample solution and place it on the device inlet.
Step 2: Wait for the sample to flow into the device columns, typically less than 20 minutes.
Step 3: Read the values of the fluid volumes, $V_o$ and $V_m$, filling up each column using the scale on the side of the column
Step 4: Compute the ratio $(V_o-V_m)/(V_m)^2$.
Step 5: Read, on the calibration plot, the analyte concentration on the horizontal axis of the calibration curve corresponding to the value of the $(V_o-V_m)/(V_m)^2$ ratio on the vertical axis.

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:

1. A method of detecting and quantifying the concentration of magnetic-responsive micro-beads in a fluid, comprising:
measuring flow rate ($Q_m$) of the fluid in at least one test micro-channel (Cm) exposed to a magnetic field gradient with flow rate ($Q_o$) of the fluid in a calibration micro-channel (Co) not exposed to a magnetic field gradient, wherein the presence of magnetic-responsive micro-beads in the at least one test micro-channel which is exposed to the magnetic field gradient causes flocculation of the magnetic-responsive micro-beads in the fluid which reduces the flow rate of the fluid through the at least one test micro-channel, wherein both micro-channels are kept at an equal and constant pressure;
calculating the ratio $Q_m/Q_o$, the difference $Q_o-Q_m$, and the ratio $(Q_o-Q_m)^p/(Q_m)^q$, wherein p and q are derived through a calibration process, and wherein the ratios $Q_m/Q_o$ and $(Q_o-Q_m)^p/(Q_m)^q$ are a proxy for the number of magnetic-responsive micro-beads in the fluid; and quantifying the concentration of magnetic-responsive micro-beads in the fluid.

2. The method of claim 1, wherein the magnetic field gradient is generated from two magnets aligned lengthwise with the at least one test micro-channel and along opposite poles to expose the at least one test micro-channel to the magnetic field gradient, said at least one test micro-channel located between a gap formed between the opposite poles of the magnets; or is generated from one magnet and a magnetic-responsive structure positioned near the at least one test micro-channel.

3. The method of claim 2, wherein the magnetic field generated is between about 0.05 Tesla (T) to about 0.5 T, and wherein the magnetic field gradient generated is about 10 T/m or greater.

4. The method of claim 1, wherein the at least one test micro-channel and the calibration micro-channel are made of a capillary tube having a length of about 0.2 cm to about 20 cm.

5. The method of claim 4, wherein the length of the capillary tube is about 1.5 cm.

6. The method of claim 1, wherein the concentration of magnetic-responsive micro-beads which can be detected and quantified is about 50 micro-beads/µl to about $2 \times 10^6$ micro-beads/µl, and wherein the diameter of the magnetic-responsive micro-beads is about 0.2 µm to about 20 µm.

7. The method of claim 6, wherein the magnetic-responsive micro-beads have a diameter of about 4.0 µm.

8. The method of claim 4, wherein the flow rate is measured in one, three or four test micro-channels, and one calibration micro-channel.

9. The method of claim 8, wherein the flow rate is measured in one test micro-channel and one calibration micro-channel, and wherein the one test micro-channel and the one calibration micro-channel have the same inner diameter of about 50 µm to about 500 µm.

10. The method of claim 9, wherein the inner diameter of the one test micro-channel and the one calibration micro-channel is about 50 µm.

11. The method of claim 8, wherein the flow rate is measured in three test micro-channels and one calibration micro-channel, wherein each of the three test micro-channels is in continuous fluid connection with one graduated column, wherein the three test micro-channels each have a different inner diameter, wherein the one calibration micro-channel has an inner diameter such that the areas of the cross-section of the one calibration micro-channel is identical to the sum of the areas of the cross-sections of the three test micro-channels, and wherein the first test micro-channel has an inner diameter of about 50 µm to about 500 µm, the second test micro-channel has an inner diameter of about 100 µm to about 250 µm, and the third test micro-channel has an inner diameter of about 250 µm to about 5 mm.

12. The method of claim 11, wherein the first test micro-channel has an inner diameter of about 50 µm, the second test micro-channel has an inner diameter of about 100 µm, and the third test micro-channel has an inner diameter of about 250 µm.

13. The method of claim 8, wherein the flow rate is measured in four test micro-channels and one calibration micro-channel, wherein the four test micro-channels merge to be in continuous fluid connection with one graduated column, wherein the four test micro-channels have the same inner diameter of about 12.5 µm to about 125 µm, and wherein the one calibration micro-channel has an inner diameter such that the areas of the cross-section of the one calibration micro-channel is identical to the sum of the areas of the cross-sections of the four test micro-channels.

14. The method of claim 13, wherein the four test micro-channels have an inner diameter of about 12.5 µm.

15. A method for detecting and quantifying concentration of an analyte in a liquid sample, comprising:

adding a liquid sample to a liquid sample inlet of a reaction chamber, said liquid sample inlet defined by an opening for accepting the liquid sample, said reaction chamber having adsorbed on its surface a plurality of immobilized antigen-specific antibodies (Ab1) specific to an analyte, said surface of the reaction chamber also having a plurality of magnetic-responsive micro-beads desiccated thereon, each of said plurality of magnetic-responsive micro-beads coated with an antigen-specific antibody (Ab2) specific to the analyte;

having the liquid sample flow through the reaction chamber causing rehydration of the plurality of antibody-coated magnetic-responsive micro-beads as the liquid sample flows through the reaction chamber, said rehydration dispersing the antibody-coated magnetic-responsive micro-beads into the liquid sample;

binding the rehydrated antibody-coated magnetic-responsive micro-beads as well as the antigen-specific antibodies immobilized on the surface of the reaction chamber to any analyte present in the liquid sample to form Ab1-analyte-Ab2-coated magnetic micro-bead complexes on the surface of the reaction chamber;

having the liquid sample containing any unbound antibody-coated magnetic micro-beads exit the reaction chamber through an reaction chamber outlet, said assay outlet in continuous fluid connection with a micro-channel splitter which bifurcates to form a calibration micro-channel (Co) and at least one test micro-channel (Cm), said at least one test micro-channel and said calibration micro-channel kept at an equal and constant pressure, said calibration micro-channel in continuous fluid connection with a graduated column, and said at least one test micro-channel in continuous fluid connection with at least one graduated column, said each of the graduated columns having a graduated scale thereon; and measuring flow rate (Qm) of the liquid sample in the at least one test micro-channel exposed to a magnetic field gradient with flow rate (Qo) of the fluid in the calibration micro-channel not exposed to a magnetic field gradient, wherein the presence of any unbound antibody-coated magnetic-responsive micro-beads in the at least one test micro-channel which is exposed to the magnetic field gradient causes flocculation of the antibody-coated magnetic-responsive micro-beads in the liquid sample which reduces the flow rate of the liquid sample through the at least one test micro-channel;

calculating the ratio $Q_m/Q_o$, the difference $Q_o-Q_m$, and the ratio $(Q_o-Q_m)^p/(Q_m)^q$, wherein p and q are derived through a calibration process, and wherein the ratios $Q_m/Q_o$ and $(Q_o-Q_m)^p/(Q_m)^q$ are a proxy for the number of magnetic-responsive micro-beads in the liquid sample, which is a proxy for the concentration of analyte in the liquid sample; and quantifying the concentration of analyte in the liquid sample.

16. The method of claim 15, wherein the magnetic field gradient is generated from two magnets aligned lengthwise with the at least one test micro-channel and along opposite poles to expose the at least one test micro-channel to the magnetic field gradient, said at least one test micro-channel located between a gap formed between the opposite poles of the magnets; or is generated from one magnet and a magnetic-responsive structure positioned near the at least one test micro-channel.

17. The method of claim 16, wherein the magnetic field generated is between about 0.05 Tesla (T) to about 0.5 T, and wherein the magnetic field gradient generated is about 10 T/m or greater.

18. The method of claim 15, wherein the at least one test micro-channel and the calibration micro-channel are made of a capillary tube having a length of about 0.2 cm to about 20 cm.

19. The method of claim 18, wherein the length of the capillary tube is about 1.5 cm.

20. The method of claim 15, wherein the concentration of magnetic-responsive micro-beads which can be detected and quantified is about 50 micro-beads/µl to about $2 \times 10^6$ micro-beads/µl, and wherein the diameter of the magnetic-responsive micro-beads is about 0.2 µm to about 20 µm.

21. The method of claim 20, wherein the magnetic-responsive micro-beads have a diameter of about 4.0 µm.

22. The method of claim 18, wherein bifurcation of the micro-channel splitter forms one, three or four test micro-channels, and one calibration micro-channel.

23. The method of claim 22, wherein bifurcation of the micro-channel splitter forms one test micro-channel and one calibration micro-channel, and wherein the one test micro-channel and the one calibration micro-channel have the same inner diameter of about 50 µm to about 500 µm.

24. The method of claim 23, wherein the inner diameter of the one test micro-channel and the one calibration micro-channel is about 50 µm.

25. The method of claim 22, wherein bifurcation of the micro-channel splitter forms three test micro-channels and one calibration micro-channel, wherein each of the three test micro-channels is in continuous fluid connection with one graduated column, wherein the three test micro-channels each have a different inner diameter, wherein the one calibration micro-channel has an inner diameter such that the areas of the cross-section of the one calibration micro-channel is identical to the sum of the areas of the cross-sections of the three test micro-channels, and wherein the first test micro-channel has an inner diameter of about 50 µm to about 500 µm, the second test micro-channel has an inner diameter of about 100 µm to about 250 µm, and the third test micro-channel has an inner diameter of about 250 µm to about 5 mm.

26. The method of claim 25, wherein the first test micro-channel has an inner diameter of about 50 µm, the second test micro-channel has an inner diameter of about 100 µm, and the third test micro-channel has an inner diameter of about 250 µm.

27. The method of claim 22, wherein bifurcation of the micro-channel splitter forms four test micro-channels and one calibration micro-channel, wherein the four test micro-channels merge to be in continuous fluid connection with one graduated column, wherein the four test micro-channels have the same inner diameter of about 12.5 µm to about 125 µm, and wherein the one calibration micro-channel has an inner diameter such that the area of the cross-section of the one calibration micro-channel is identical to the sum of the areas of the cross-sections of the four test micro-channels.

28. The method of claim 27, wherein the four test micro-channels have an inner diameter of about 12.5 µm.

29. The method of claim 15, wherein the analyte is selected from the group consisting of proteins, protein fragments, antigens, antibodies, antibody fragments, peptides, RNA, RNA fragments, functionalized magnetic micro-beads specific to $CD^{4+}$, $CD^{8+}$ cells, malaria-infected red blood cells, cancer cells, cancer biomarkers such as prostate specific antigen and other cancer biomarkers, viruses, bacteria such as *E. coli*, and other pathogenic agents.

\* \* \* \* \*